(12) United States Patent
Yanaki

(10) Patent No.: US 8,197,844 B2
(45) Date of Patent: Jun. 12, 2012

(54) ACTIVE ELECTRODE FOR TRANSDERMAL MEDICAMENT ADMINISTRATION

(75) Inventor: Jamal S. Yanaki, Salt Lake City, UT (US)

(73) Assignee: Activatek, Inc., Salt Lake City, UT (US)

( * ) Notice: Subject to any disclaimer, the term of this patent is extended or adjusted under 35 U.S.C. 154(b) by 1320 days.

(21) Appl. No.: 11/811,241

(22) Filed: Jun. 8, 2007

(65) Prior Publication Data
US 2008/0305154 A1   Dec. 11, 2008

(51) Int. Cl.
*A61F 13/00* (2006.01)
*A61F 13/02* (2006.01)
*A61B 5/04* (2006.01)

(52) U.S. Cl. ......... 424/449; 424/448; 600/386; 600/391

(58) Field of Classification Search .......... 604/20, 604/891.1, 892.1; 424/448–449; 600/386, 600/391
See application file for complete search history.

(56) References Cited

U.S. PATENT DOCUMENTS

| | | | |
|---|---|---|---|
| 1,967,927 A | 7/1934 | Deutsch | 174/89 |
| 2,784,715 A | 3/1957 | Kestler | 128/172.1 |
| 3,289,671 A | 12/1966 | Troutman et al. | 128/2.1 |
| 3,604,417 A | 9/1971 | Stolzenberg | 128/213 |
| 3,618,601 A | 11/1971 | Richardson | 128/2.1 R |

(Continued)

FOREIGN PATENT DOCUMENTS
EP              931564               7/1999
(Continued)

OTHER PUBLICATIONS

Empi, "Action Patch, the Smart Iontophoresis System™" product literature, available at http://www.empi.com/products/ionot.cfm (accessed Oct. 4, 2005).

(Continued)

*Primary Examiner* — (Jackie) Tan-Uyen T. Ho
*Assistant Examiner* — Michael J Anderson
(74) *Attorney, Agent, or Firm* — Kirton McConkie; F. Chad Copier

(57) ABSTRACT

A transdermal medicament patch includes a biocompatible substrate having a therapeutic face on one side configured for disposition against the skin of a patient, a biocompatible adhesive on the therapeutic face, a planar medicament matrix covering a portion of the therapeutic face, and a release liner covering the portion of therapeutic that is not obscured by the medicament matrix. An aperture formed through the release sheet affords direct access by medicament to the entire surface of the medicament matrix opposite from the therapeutic face of the substrate. An active electrode positioned between the medicament matrix and the therapeutic face of the substrate includes an electrically conductive backing layer positioned against the therapeutic face of the substrate and a pH-control layer covering less than all of the side of the backing layer opposite from the therapeutic face of the substrate. One active electrode design criterion relates the relative size of the pH-control layer to the size of the backing layer; another relates the size of portion of the area of the backing layer that is free of the pH-control lawyer to the size of the pH-control layer. The pH-control layer is made of an electrically conductive material capable of moderating changes in the hydrogen-ion concentration in the medicament matrix during iontophoretic current flow. An electrical contact electrically coupled through the substrate to the backing layer includes a hollow, electrically conductive snap fitting having an open end and a cooperating stud that is inserted into the open end of the snap.

36 Claims, 9 Drawing Sheets

U.S. PATENT DOCUMENTS

| | | | | |
|---|---|---|---|---|
| 3,760,805 A | 9/1973 | Higuchi | | 128/260 |
| 3,760,984 A | 9/1973 | Theeuwes | | 222/95 |
| 3,797,494 A | 3/1974 | Zaffaroni | | 128/268 |
| 3,991,755 A | 11/1976 | Vernon et al. | | 128/172.1 |
| 3,995,631 A | 12/1976 | Higuchi et al. | | 128/260 |
| 4,003,379 A | 1/1977 | Ellinwood, Jr. | | 128/260 |
| 4,034,756 A | 7/1977 | Higuchi et al. | | 128/260 |
| 4,140,122 A | 2/1979 | Kuhl et al. | | 128/260 |
| 4,141,359 A | 2/1979 | Jacobsen et al. | | 128/172.1 |
| 4,240,884 A | 12/1980 | Pellegri | | 204/95 |
| 4,250,878 A | 2/1981 | Jacobsen et al. | | 128/207.21 |
| 4,292,968 A | 10/1981 | Ellis | | 128/207.21 |
| 4,325,367 A | 4/1982 | Tapper | | 128/207.21 |
| 4,383,529 A | 5/1983 | Webster | | 604/20 |
| 4,406,658 A | 9/1983 | Lattin et al. | | 604/20 |
| 4,416,274 A | 11/1983 | Jacobsen et al. | | 604/20 |
| 4,452,249 A | 6/1984 | Sachs et al. | | 28/642 |
| 4,474,570 A | 10/1984 | Ariura et al. | | 604/20 |
| 4,522,698 A | 6/1985 | Maget | | 204/301 |
| 4,539,004 A | 9/1985 | Eckenhoff et al. | | 604/131 |
| 4,557,723 A | 12/1985 | Sibalis | | 604/20 |
| H71 H | 6/1986 | Sorenson et al. | | 604/20 |
| 4,619,654 A | 10/1986 | Abplanalp | | 604/20 |
| 4,622,031 A | 11/1986 | Sibalis | | 604/20 |
| 4,627,429 A | 12/1986 | Tsuk | | 128/156 |
| 4,702,732 A | 10/1987 | Powers et al. | | 604/20 |
| 4,708,716 A | 11/1987 | Sibalis | | 604/20 |
| 4,713,050 A | 12/1987 | Sibalis | | 604/20 |
| 4,722,726 A | 2/1988 | Sanderson et al. | | 604/20 |
| 4,725,263 A | 2/1988 | McNichols et al. | | 604/20 |
| 4,731,049 A | 3/1988 | Parsi | | 604/20 |
| 4,731,926 A | 3/1988 | Sibalis | | 604/20 |
| 4,734,090 A | 3/1988 | Sibalis | | 604/20 |
| D296,006 S | 5/1988 | Asche | | D24/63 |
| 4,744,787 A | 5/1988 | Phipps et al. | | 604/20 |
| 4,747,819 A | 5/1988 | Phipps et al. | | 604/20 |
| 4,752,285 A | 6/1988 | Petelenz | | 604/20 |
| RE32,724 E | 8/1988 | Cartmell | | 128/640 |
| 4,764,164 A | 8/1988 | Sasaki | | 604/20 |
| 4,767,401 A | 8/1988 | Seiderman | | 604/20 |
| H516 H | 9/1988 | Lattin et al. | | 604/20 |
| 4,786,277 A | 11/1988 | Powers et al. | | 604/20 |
| 4,798,642 A * | 1/1989 | Craighead et al. | | 156/252 |
| 4,820,263 A | 4/1989 | Spevak et al. | | 604/20 |
| 4,822,334 A | 4/1989 | Tapper | | 604/20 |
| 4,842,577 A | 6/1989 | Konno et al. | | 604/20 |
| 4,856,188 A | 8/1989 | Sibalis | | 604/20 |
| 4,865,582 A | 9/1989 | Sibalis | | 604/20 |
| 4,878,892 A | 11/1989 | Sibalis et al. | | 604/20 |
| 4,883,457 A | 11/1989 | Sibalis | | 604/20 |
| 4,886,489 A | 12/1989 | Jacobsen et al. | | 604/20 |
| 4,886,514 A | 12/1989 | Maget | | 604/891.1 |
| 4,911,688 A | 3/1990 | Jones | | 604/20 |
| 4,915,685 A | 4/1990 | Petelenz | | 604/20 |
| 4,919,648 A | 4/1990 | Sibalis | | 604/20 |
| 4,921,475 A | 5/1990 | Sibalis | | 604/20 |
| 4,927,408 A | 5/1990 | Haak et al. | | 604/20 |
| 4,929,233 A | 5/1990 | Roth et al. | | 604/131 |
| 4,931,046 A | 6/1990 | Newman | | 604/20 |
| 4,940,456 A | 7/1990 | Sibalis et al. | | 604/20 |
| 4,942,883 A | 7/1990 | Newman | | 604/20 |
| 4,950,229 A | 8/1990 | Sage, Jr. | | 604/20 |
| 4,955,378 A | 9/1990 | Grasso | | 128/421 |
| 4,973,303 A | 11/1990 | Johnson et al. | | 604/20 |
| 5,002,527 A | 3/1991 | Reller et al. | | 604/20 |
| 5,013,293 A | 5/1991 | Sibalis | | 604/20 |
| 5,032,109 A | 7/1991 | Sibalis | | 604/20 |
| 5,032,110 A | 7/1991 | Watanabe | | 604/20 |
| 5,035,711 A | 7/1991 | Aoki | | 623/11 |
| 5,037,381 A | 8/1991 | Bock | | 604/20 |
| 5,041,107 A | 8/1991 | Heil, Jr. | | 604/891.1 |
| 5,042,975 A | 8/1991 | Chien et al. | | 604/20 |
| 5,047,007 A | 9/1991 | McNichols et al. | | 604/20 |
| 5,053,001 A | 10/1991 | Reller et al. | | 604/20 |
| 5,057,072 A | 10/1991 | Phipps | | 604/20 |
| 5,063,175 A | 11/1991 | Broadbent | | 437/192 |
| 5,080,646 A | 1/1992 | Theeuwes et al. | | 604/20 |
| 5,084,006 A | 1/1992 | Lew et al. | | 604/20 |
| 5,084,008 A | 1/1992 | Phipps | | 604/20 |
| 5,087,240 A | 2/1992 | Sibalis | | 604/20 |
| 5,087,242 A | 2/1992 | Petelenz et al. | | 604/20 |
| 5,088,977 A | 2/1992 | Sibalis | | 604/20 |
| 5,088,978 A | 2/1992 | Hillman et al. | | 604/20 |
| 5,109,847 A | 5/1992 | Liss et al. | | 128/421 |
| 5,125,894 A | 6/1992 | Phipps et al. | | 604/20 |
| 5,135,477 A | 8/1992 | Untereker et al. | | 604/20 |
| 5,135,478 A | 8/1992 | Sibalis | | 604/20 |
| 5,135,479 A * | 8/1992 | Sibalis et al. | | 604/20 |
| 5,135,480 A | 8/1992 | Bannon | | 604/20 |
| 5,147,296 A | 9/1992 | Theeuwes et al. | | 604/20 |
| 5,147,297 A | 9/1992 | Myers et al. | | 604/20 |
| 5,152,758 A | 10/1992 | Kaetsu et al. | | 604/890.1 |
| 5,156,591 A | 10/1992 | Gross et al. | | 604/20 |
| 5,158,537 A | 10/1992 | Haak et al. | | 604/20 |
| 5,160,316 A | 11/1992 | Henley | | 604/20 |
| 5,162,042 A | 11/1992 | Gyory et al. | | 604/20 |
| 5,162,043 A | 11/1992 | Lew et al. | | 604/20 |
| 5,163,899 A | 11/1992 | Sibalis | | 604/20 |
| 5,167,616 A | 12/1992 | Haak et al. | | 604/20 |
| 5,167,617 A | 12/1992 | Sibalis | | 604/20 |
| 5,169,382 A | 12/1992 | Theeuwes et al. | | 604/20 |
| 5,169,383 A | 12/1992 | Gyory et al. | | 604/20 |
| 5,203,768 A | 4/1993 | Haak et al. | | 604/20 |
| 5,207,752 A | 5/1993 | Sorenson et al. | | 604/20 |
| 5,221,254 A | 6/1993 | Phipps | | 604/20 |
| 5,224,928 A | 7/1993 | Sibalis et al. | | 604/20 |
| 5,232,438 A | 8/1993 | Theeuwes et al. | | 604/20 |
| 5,234,992 A | 8/1993 | Gyory et al. | | 525/87 |
| 5,236,412 A | 8/1993 | Lloyd et al. | | 604/20 |
| 5,240,995 A | 8/1993 | Gyory et al. | | 525/57 |
| 5,246,417 A | 9/1993 | Haak et al. | | 604/20 |
| 5,246,418 A | 9/1993 | Haynes et al. | | 604/20 |
| 5,248,295 A | 9/1993 | Jacobsen et al. | | 604/20 |
| 5,250,022 A | 10/1993 | Chien et al. | | 604/20 |
| 5,250,023 A | 10/1993 | Lee et al. | | 604/20 |
| 5,254,081 A | 10/1993 | Maurer et al. | | 604/20 |
| 5,256,137 A | 10/1993 | Sage, Jr. | | 604/20 |
| 5,281,287 A | 1/1994 | Lloyd et al. | | 156/80 |
| 5,284,471 A | 2/1994 | Sage, Jr. | | 604/20 |
| 5,286,254 A | 2/1994 | Shapland et al. | | 604/21 |
| 5,295,482 A | 3/1994 | Clare et al. | | 128/639 |
| 5,298,017 A | 3/1994 | Theeuwes et al. | | 604/20 |
| 5,306,235 A | 4/1994 | Haynes | | 604/20 |
| 5,310,403 A | 5/1994 | Haynes | | 604/20 |
| 5,310,404 A | 5/1994 | Gyory et al. | | 604/20 |
| 5,312,326 A | 5/1994 | Myers et al. | | 604/20 |
| 5,314,502 A | 5/1994 | McNichols et al. | | 604/20 |
| 5,320,597 A | 6/1994 | Sage, Jr. et al. | | 604/20 |
| 5,320,598 A | 6/1994 | Haak et al. | | 604/20 |
| 5,320,731 A | 6/1994 | Muller et al. | | 204/299 R |
| 5,322,502 A | 6/1994 | Theeuwes et al. | | 604/20 |
| 5,326,341 A | 7/1994 | Lew et al. | | 604/20 |
| 5,328,452 A | 7/1994 | Sibalis | | 604/20 |
| 5,328,453 A | 7/1994 | Sibalis | | 604/20 |
| 5,328,455 A | 7/1994 | Llyod et al. | | 604/20 |
| 5,344,394 A | 9/1994 | Gyory et al. | | 604/20 |
| 5,356,632 A | 10/1994 | Gross et al. | | 424/449 |
| 5,358,483 A | 10/1994 | Sibalis | | 604/20 |
| 5,362,308 A | 11/1994 | Chien et al. | | 604/20 |
| 5,374,241 A | 12/1994 | Lloyd et al. | | 604/20 |
| 5,374,242 A | 12/1994 | Haak et al. | | 604/20 |
| 5,376,107 A | 12/1994 | Inagi et al. | | 607/75 |
| 5,380,271 A | 1/1995 | Gyory | | 604/20 |
| 5,380,272 A | 1/1995 | Gross | | 604/20 |
| 5,385,543 A | 1/1995 | Haak et al. | | 604/20 |
| 5,387,189 A | 2/1995 | Gory et al. | | 604/20 |
| 5,395,310 A | 3/1995 | Untereker et al. | | 604/20 |
| 5,403,275 A | 4/1995 | Phipps | | 604/20 |
| 5,405,614 A | 4/1995 | D'Angelo et al. | | 424/449 |
| 5,413,572 A | 5/1995 | Wong et al. | | 604/892.1 |
| 5,415,628 A | 5/1995 | Untereker et al. | | 604/20 |
| 5,415,629 A | 5/1995 | Henley | | 604/20 |
| 5,421,817 A | 6/1995 | Liss et al. | | 604/20 |
| 5,423,739 A | 6/1995 | Phipps et al. | | 604/20 |
| 5,427,870 A | 6/1995 | Joshi et al. | | 429/27 |
| 5,431,625 A | 7/1995 | Fabian et al. | | 604/20 |
| 5,443,442 A | 8/1995 | Phipps et al. | | 604/20 |

| | | | | | | | |
|---|---|---|---|---|---|---|---|
| 5,445,606 A | 8/1995 | Haak et al. | 604/20 | 5,871,460 A | 2/1999 | Phipps et al. | 604/20 |
| 5,445,607 A | 8/1995 | Venkateshwaran et al. | 604/20 | 5,871,461 A | 2/1999 | Atanasoska et al. | 604/20 |
| 5,445,609 A | 8/1995 | Lattin et al. | 604/20 | 5,873,850 A | 2/1999 | Flower et al. | 604/20 |
| 5,450,845 A | 9/1995 | Axelgaard | 128/640 | 5,876,368 A | 3/1999 | Flower | 604/20 |
| 5,454,922 A | 10/1995 | Joshi et al. | 204/265 | 5,876,741 A | 3/1999 | Ron | 424/423 |
| 5,458,569 A | 10/1995 | Kirk, III et al. | 604/20 | 5,879,322 A | 3/1999 | Lattin et al. | 604/20 |
| 5,464,387 A | 11/1995 | Haak et al. | 604/20 | 5,899,876 A | 5/1999 | Flower | 604/120 |
| 5,466,217 A | 11/1995 | Myers et al. | 604/20 | 5,908,400 A | 6/1999 | Higo et al. | 604/20 |
| 5,492,534 A | 2/1996 | Athayde et al. | 604/141 | 5,911,223 A | 6/1999 | Weaver et al. | 128/898 |
| 5,496,266 A | 3/1996 | Haak et al. | 604/20 | 5,919,155 A | 7/1999 | Lattin et al. | 604/20 |
| 5,498,235 A | 3/1996 | Flower | 604/20 | 5,928,185 A | 7/1999 | Muller et al. | 604/20 |
| 5,499,967 A | 3/1996 | Teillaud et al. | 604/20 | 5,931,804 A | 8/1999 | Sibalis | 604/20 |
| 5,503,632 A | 4/1996 | Haak | 604/20 | 5,935,598 A | 8/1999 | Sage et al. | 424/449 |
| 5,520,180 A | 5/1996 | Uy et al. | 128/640 | 5,941,843 A | 8/1999 | Atanasoska et al. | 604/20 |
| D372,097 S | 7/1996 | Albert et al. | D24/189 | 5,944,685 A | 8/1999 | Muroki | 604/20 |
| 5,533,971 A | 7/1996 | Phipps | 604/20 | 5,947,920 A | 9/1999 | Beck | 604/20 |
| 5,533,972 A | 7/1996 | Gyory et al. | 604/20 | 5,954,268 A | 9/1999 | Joshi et al. | 293/34 |
| 5,538,503 A | 7/1996 | Henley | 604/20 | 5,971,722 A | 10/1999 | Maget | 417/379 |
| 5,540,654 A | 7/1996 | Riviere et al. | 604/20 | 5,976,101 A | 11/1999 | Sibalis | 604/20 |
| 5,540,669 A | 7/1996 | Sage, Jr. et al. | 604/20 | 5,978,701 A * | 11/1999 | Johnson et al. | 604/20 |
| 5,543,098 A | 8/1996 | Myers et al. | 264/104 | 5,983,130 A | 11/1999 | Phipps et al. | 604/20 |
| 5,558,632 A | 9/1996 | Lloyd et al. | 604/20 | 5,983,133 A | 11/1999 | Garde et al. | 604/20 |
| 5,558,633 A | 9/1996 | Phipps et al. | 604/20 | 5,990,179 A * | 11/1999 | Gyory et al. | 514/329 |
| 5,562,607 A | 10/1996 | Gyory | 604/20 | 5,991,655 A | 11/1999 | Gross et al. | 604/20 |
| 5,571,149 A | 11/1996 | Liss et al. | 607/72 | 5,993,435 A | 11/1999 | Haak et al. | 604/501 |
| 5,582,586 A | 12/1996 | Tachibana et al. | 604/20 | 5,995,869 A | 11/1999 | Cormier et al. | 604/20 |
| 5,582,587 A | 12/1996 | Gyory et al. | 604/20 | 6,004,309 A | 12/1999 | Phipps | 604/501 |
| 5,591,123 A | 1/1997 | Sibalis | 604/20 | 6,009,344 A | 12/1999 | Flower et al. | 604/20 |
| 5,603,693 A | 2/1997 | Frenkel et al. | 604/20 | 6,018,680 A | 1/2000 | Flower | 604/20 |
| 5,605,536 A | 2/1997 | Sibalis | 604/20 | 6,020,083 A | 2/2000 | Breault et al. | 492/36 |
| 5,618,265 A | 4/1997 | Myers et al. | 604/20 | 6,032,073 A | 2/2000 | Effenhauser | 604/20 |
| 5,622,530 A | 4/1997 | Phipps | 604/20 | 6,035,234 A * | 3/2000 | Riddle et al. | 604/20 |
| 5,628,729 A | 5/1997 | Okabe | 604/20 | 6,038,485 A | 3/2000 | Axelgaard | 607/148 |
| 5,645,526 A | 7/1997 | Flower | 604/20 | 6,047,208 A | 4/2000 | Flower | 604/20 |
| 5,645,527 A | 7/1997 | Beck | 604/20 | 6,050,988 A | 4/2000 | Zuck | 604/890.1 |
| 5,647,844 A | 7/1997 | Haak et al. | 604/20 | 6,057,374 A | 5/2000 | Huntington et al. | 514/772 |
| 5,651,768 A | 7/1997 | Sibalis | 604/20 | 6,064,908 A | 5/2000 | Muller et al. | 604/20 |
| 5,653,682 A | 8/1997 | Sibalis | 604/20 | 6,078,842 A | 6/2000 | Gross et al. | 607/152 |
| 5,660,177 A * | 8/1997 | Faupel et al. | 600/382 | 6,086,572 A | 7/2000 | Johnson et al. | 604/503 |
| 5,667,487 A | 9/1997 | Henley | 604/20 | 6,090,095 A | 7/2000 | McNichols et al. | 604/501 |
| 5,668,170 A | 9/1997 | Gyory | 514/449 | 6,104,951 A | 8/2000 | Mori et al. | 604/20 |
| 5,672,167 A | 9/1997 | Athayde et al. | 604/829.1 | 6,107,777 A | 8/2000 | Garde et al. | 320/122 |
| 5,681,580 A | 10/1997 | Jang et al. | 424/449 | 6,119,036 A | 9/2000 | Allen, Jr. | 604/20 |
| 5,685,837 A | 11/1997 | Horstmann | 604/20 | 6,122,554 A | 9/2000 | Coral et al. | 607/153 |
| 5,688,231 A | 11/1997 | Flower | 604/20 | 6,129,696 A | 10/2000 | Sibalis | 604/20 |
| 5,688,232 A | 11/1997 | Flower | 604/20 | 6,141,582 A | 10/2000 | Mori et al. | 604/20 |
| 5,693,010 A | 12/1997 | Ledger et al. | 604/20 | 6,157,858 A | 12/2000 | Gross et al. | 604/20 |
| 5,693,024 A | 12/1997 | Flower | 604/20 | 6,163,720 A | 12/2000 | Gyory et al. | 604/20 |
| 5,697,896 A | 12/1997 | McNichols et al. | 604/20 | 6,167,301 A | 12/2000 | Flower et al. | 604/20 |
| 5,700,481 A | 12/1997 | Iga et al. | 424/449 | 6,167,302 A | 12/2000 | Millot | 604/20 |
| 5,711,761 A | 1/1998 | Untereker et al. | 604/20 | 6,169,920 B1 | 1/2001 | Haak et al. | 604/20 |
| 5,713,846 A | 2/1998 | Bernhard et al. | 604/20 | 6,171,294 B1 | 1/2001 | Southam et al. | 604/501 |
| 5,718,913 A | 2/1998 | Dhuique-Mayer et al. | 424/449 | 6,175,763 B1 | 1/2001 | Sorenson et al. | 604/20 |
| 5,730,716 A | 3/1998 | Beck et al. | 604/20 | 6,181,963 B1 | 1/2001 | Chin et al. | 604/20 |
| 5,735,897 A | 4/1998 | Buirge | 623/12 | 6,192,270 B1 | 2/2001 | Hofmann et al. | 604/20 |
| 5,736,153 A | 4/1998 | Lamers | 424/449 | 6,195,582 B1 | 2/2001 | Scott | 604/20 |
| 5,738,647 A | 4/1998 | Bernhard et al. | 604/20 | 6,198,955 B1 | 3/2001 | Axelgaard et al. | 600/391 |
| 5,746,711 A | 5/1998 | Sibalis et al. | 604/20 | 6,208,891 B1 | 3/2001 | Flower | 604/20 |
| 5,766,144 A | 6/1998 | Lai et al. | 604/20 | 6,216,033 B1 | 4/2001 | Southam et al. | 604/503 |
| 5,771,890 A | 6/1998 | Tamada | 128/635 | 6,219,576 B1 | 4/2001 | Gupta et al. | 604/20 |
| 5,772,688 A | 6/1998 | Muroki | 607/1 | 6,223,075 B1 | 4/2001 | Beck et al. | 604/20 |
| 5,785,040 A | 7/1998 | Axelgaard | 128/640 | 6,246,904 B1 | 6/2001 | Murdock | 604/20 |
| 5,788,666 A | 8/1998 | Atanasoska | 604/20 | 6,259,946 B1 | 7/2001 | Higo et al. | 604/20 |
| 5,795,321 A | 8/1998 | McArthur et al. | 604/20 | 6,261,595 B1 | 7/2001 | Stanley et al. | 424/449 |
| 5,797,867 A | 8/1998 | Guerrera et al. | 604/20 | 6,289,241 B1 | 9/2001 | Phipps | 604/20 |
| 5,807,305 A | 9/1998 | Muller et al. | 604/20 | 6,289,242 B1 | 9/2001 | Phipps et al. | 604/20 |
| 5,817,044 A | 10/1998 | Evers et al. | 604/20 | 6,295,469 B1 | 9/2001 | Linkwitz et al. | 604/20 |
| 5,830,175 A | 11/1998 | Flower | 604/20 | 6,317,629 B1 | 11/2001 | Haak et al. | 604/20 |
| 5,833,665 A | 11/1998 | Bootman et al. | 604/180 | 6,324,424 B1 | 11/2001 | Ledger et al. | 604/20 |
| 5,840,056 A | 11/1998 | Atanasoska | 604/20 | 6,327,496 B1 * | 12/2001 | Hamlin et al. | 604/20 |
| 5,843,014 A | 12/1998 | Lattin et al. | 604/20 | 6,330,471 B1 | 12/2001 | Higo et al. | 604/20 |
| 5,846,217 A | 12/1998 | Beck et al. | 604/20 | 6,333,189 B1 | 12/2001 | Holladay et al. | 435/283.1 |
| 5,848,985 A | 12/1998 | Muroki | 604/20 | 6,336,049 B1 | 1/2002 | Kinbara et al. | 607/148 |
| 5,857,992 A | 1/1999 | Haak et al. | 604/20 | 6,355,025 B1 | 3/2002 | Phipps et al. | 604/501 |
| 5,857,993 A | 1/1999 | Atanasoska et al. | 604/20 | 6,374,136 B1 | 4/2002 | Murdock | 604/20 |
| 5,857,994 A | 1/1999 | Flower | 604/20 | 6,377,847 B1 | 4/2002 | Keusch et al. | 604/20 |
| 5,865,786 A | 2/1999 | Sibalis et al. | 604/20 | 6,377,848 B1 | 4/2002 | Garde et al. | 604/20 |
| 5,865,792 A | 2/1999 | Ledger et al. | 604/20 | 6,385,488 B1 | 5/2002 | Flower et al. | 604/20 |
| 5,869,078 A | 2/1999 | Baudino | 424/423 | 6,418,333 B1 | 7/2002 | Axelgaard | 600/391 |

| Patent | Date | Inventor | Class |
|---|---|---|---|
| 6,421,561 B1 | 7/2002 | Morris | 604/20 |
| 6,424,862 B1 | 7/2002 | Brown, III et al. | 604/20 |
| 6,453,205 B1 * | 9/2002 | Dupelle et al. | 607/152 |
| 6,477,411 B1 | 11/2002 | Beck | 604/20 |
| 6,488,959 B2 | 12/2002 | Stanley et al. | 424/449 |
| 6,496,727 B1 | 12/2002 | Bernhard et al. | 604/20 |
| 6,505,069 B2 | 1/2003 | Scott et al. | 604/20 |
| 6,522,919 B1 | 2/2003 | Flower et al. | 604/20 |
| 6,546,284 B2 | 4/2003 | Plummer | 604/20 |
| 6,560,483 B1 | 5/2003 | Kumar et al. | 604/20 |
| 6,564,092 B1 | 5/2003 | Nakamura et al. | 604/20 |
| 6,567,693 B1 | 5/2003 | Allen, Jr. | 604/20 |
| 6,584,349 B1 | 6/2003 | Sage, Jr. et al. | 604/20 |
| 6,587,717 B1 | 7/2003 | Kuribayashi et al. | 604/20 |
| 6,591,133 B1 | 7/2003 | Joshi | 604/21 |
| 6,615,079 B1 | 9/2003 | Avrahami | 604/20 |
| 6,622,037 B2 | 9/2003 | Kasano | 604/20 |
| 6,629,968 B1 | 10/2003 | Jain et al. | 604/501 |
| 6,635,045 B2 | 10/2003 | Keusch et al. | 604/501 |
| 6,643,532 B2 | 11/2003 | Axelgaard | 600/391 |
| 6,643,544 B1 | 11/2003 | Adachi et al. | 604/20 |
| 6,650,934 B2 | 11/2003 | Murdock | 604/20 |
| 6,653,014 B2 | 11/2003 | Anderson et al. | 429/122 |
| 6,654,635 B1 | 11/2003 | Koga et al. | 604/20 |
| 6,662,044 B2 | 12/2003 | Crawford | 604/20 |
| 6,673,852 B1 | 1/2004 | Suda et al. | 523/105 |
| 6,678,555 B2 | 1/2004 | Flower et al. | 604/20 |
| 6,687,522 B2 * | 2/2004 | Tamada | 600/347 |
| 6,687,537 B2 | 2/2004 | Bernabei | 604/20 |
| 6,718,201 B1 | 4/2004 | Phipps et al. | 604/20 |
| 6,725,090 B1 | 4/2004 | Lattin et al. | 604/20 |
| 6,731,977 B2 | 5/2004 | Beck | 604/20 |
| 6,735,470 B2 | 5/2004 | Henley et al. | 604/20 |
| 6,738,662 B1 | 5/2004 | Frank | 604/20 |
| 6,743,432 B1 | 6/2004 | Yanai et al. | 424/400 |
| 6,745,071 B1 | 6/2004 | Anderson et al. | 604/20 |
| 6,748,265 B2 | 6/2004 | Hoffmann et al. | 604/20 |
| 6,748,266 B2 | 6/2004 | Bernabei | 604/20 |
| 6,757,560 B1 | 6/2004 | Fischer et al. | 604/20 |
| 6,767,632 B2 | 7/2004 | Axelgaard | 428/355 RA |
| 6,775,569 B2 | 8/2004 | Mori et al. | 604/20 |
| 6,775,570 B2 | 8/2004 | Joshi | 604/20 |
| 6,792,306 B2 | 9/2004 | Henley et al. | 604/20 |
| 6,842,636 B2 | 1/2005 | Perrault et al. | 600/391 |
| 6,842,640 B2 | 1/2005 | Riddle et al. | 604/20 |
| 6,862,473 B2 | 3/2005 | Keusch et al. | 604/20 |
| 6,895,271 B2 | 5/2005 | Henley | 604/20 |
| 6,915,159 B1 | 7/2005 | Kuribayashi et al. | 604/20 |
| 6,947,791 B2 | 9/2005 | Zhang et al. | 604/20 |
| 6,970,739 B1 | 11/2005 | Inoue | 604/20 |
| 7,016,724 B2 | 3/2006 | Henley et al. | 604/20 |
| 7,045,559 B2 | 5/2006 | Yahiaoui et al. | 523/111 |
| 7,047,069 B2 | 5/2006 | Joshi | 604/20 |
| 7,069,073 B2 | 6/2006 | Henley et al. | 604/20 |
| 7,187,985 B2 | 3/2007 | Carim | 607/152 |
| 7,252,792 B2 | 8/2007 | Perrault et al. | 252/500 |
| 7,340,310 B2 | 3/2008 | Nitzan et al. | 607/129 |
| D576,282 S | 9/2008 | Yanaki | D24/189 |
| 7,476,221 B2 | 1/2009 | Sun et al. | 604/501 |
| 2002/0055704 A1 * | 5/2002 | Scott et al. | 604/20 |
| 2002/0182485 A1 | 12/2002 | Anderson et al. | 429/105 |
| 2003/0088204 A1 | 5/2003 | Joshi | 604/20 |
| 2003/0149393 A1 | 8/2003 | Joshi | 604/20 |
| 2003/0149394 A1 | 8/2003 | Joshi | 604/20 |
| 2004/0143210 A1 | 7/2004 | Shevlin | 604/20 |
| 2004/0225253 A1 | 11/2004 | Shevlin | 604/20 |
| 2004/0267237 A1 | 12/2004 | Sun et al. | 604/501 |
| 2005/0010192 A1 | 1/2005 | Sun et al. | 604/501 |
| 2005/0143686 A1 | 6/2005 | Shevlin | 604/20 |
| 2005/0148996 A1 * | 7/2005 | Sun et al. | 604/501 |
| 2006/0229549 A1 | 10/2006 | Hause, Jr. et al. | 604/20 |
| 2007/0093788 A1 | 4/2007 | Carter | 604/890.1 |
| 2008/0004564 A1 | 1/2008 | Smith | 604/20 |
| 2008/0177219 A1 | 7/2008 | Joshi | 604/20 |
| 2008/0188791 A1 | 8/2008 | DiFiore et al. | 604/20 |
| 2008/0214985 A1 | 9/2008 | Yanaki | 604/20 |
| 2008/0305154 A1 | 12/2008 | Yanaki | 424/449 |
| 2009/0186072 A1 | 7/2009 | Yanaki | 424/449 |
| 2010/0106075 A1 | 4/2010 | Joshi | 604/20 |
| 2011/0160639 A1 | 6/2011 | Yanaki | 604/20 |

FOREIGN PATENT DOCUMENTS

| | | |
|---|---|---|
| WO | 2007/064722 | 6/2007 |
| WO | WO 2007064722 A1 * | 6/2007 |
| WO | 2008/091671 | 7/2008 |
| WO | 2008/153931 | 12/2008 |
| WO | 2009/091372 | 7/2009 |
| WO | 2010/002363 | 1/2010 |

OTHER PUBLICATIONS

Empi, "Important Features of DUPEL B.L.U.E.™" product literature © 2002, available at http://www.empi.com/products/ionto/dupel2.pdf (accessed Oct. 4, 2005).

Eemso, E-Strip product sample (acquired circa Oct. 2005).

Iomed, Inc., "Iomed® First in Iontophoresis" trade literature © 2005, available at http://www.iomed.com/pdf/iomed%brochure%20rev0C.pdf (accessed Oct. 4, 2005).

Iomed, Inc., "Quality . . . Measured in Outcomes" product literature © 2005, available at http://www.iomed.com/ (accessed Oct. 4, 2005).

Iomed, Inc., Iogel™ product system sample components (acquired circa Oct. 2005).

Iomed, Inc., Companion 80™ product sample (acquired circa Oct. 2005).

Travanti Pharma, Inc., "IontoPatch® Device" product literature © 2002, available ahttp://www.travantipharma.com/markets__iontioatch__device.html (accessed Oct. 4, 2005).

Travanti Pharma, Inc., "IontoPatch™—Iontophoresis with the Battery Built-in" product literature, available at http://www.travantipharma.com/pdf/IontoPatch__info.pdf (accessed Oct. 4, 2005).

Travanti Pharma, Inc., IontoPatch® product sample (acquired circa Oct. 2005.

Travanti Pharma, Inc., "WEDD® Strengths" product literature © 2002, available at http://www.travantipharma.com/technology__strengths.html (accessed Oct. 4, 2005).

Travanti Pharma, Inc., "WEDD® Targets" product literature © 2002, available at http://www.travantipharma.com/market__targets.html (accessed Oct. 4, 2005).

Travanti Pharma, Inc., "WEDD® Wearable Electronic Disposable Drug Delivery" product literature © 2002, available at http://www.travantipharma.com/ (accessed Oct. 4, 2005).

Warden, Glenn D., "Electrical Safety in Iontophoresis", 20 *Rehab Mgmt* 20-23 (Mar. 2007).

* cited by examiner

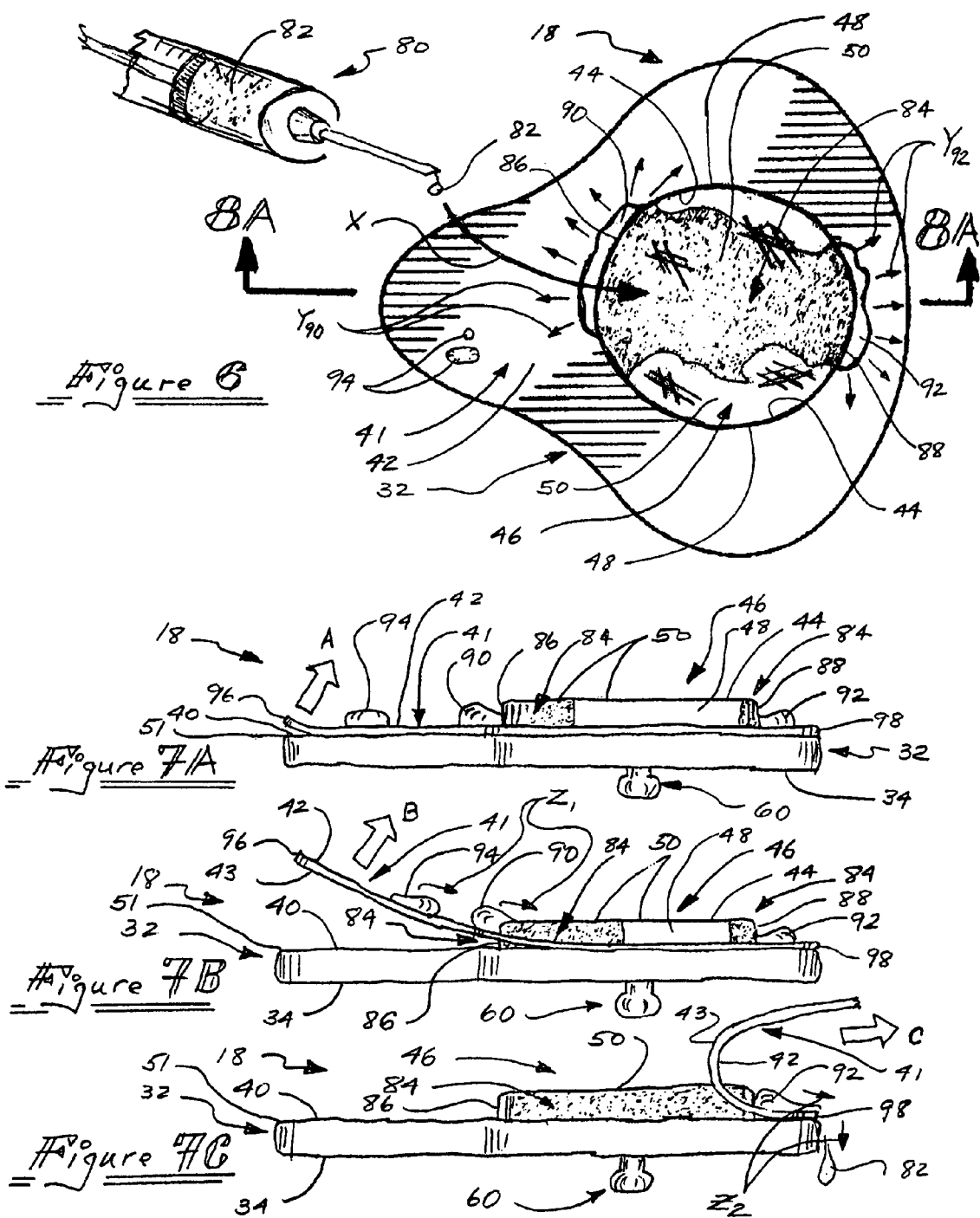

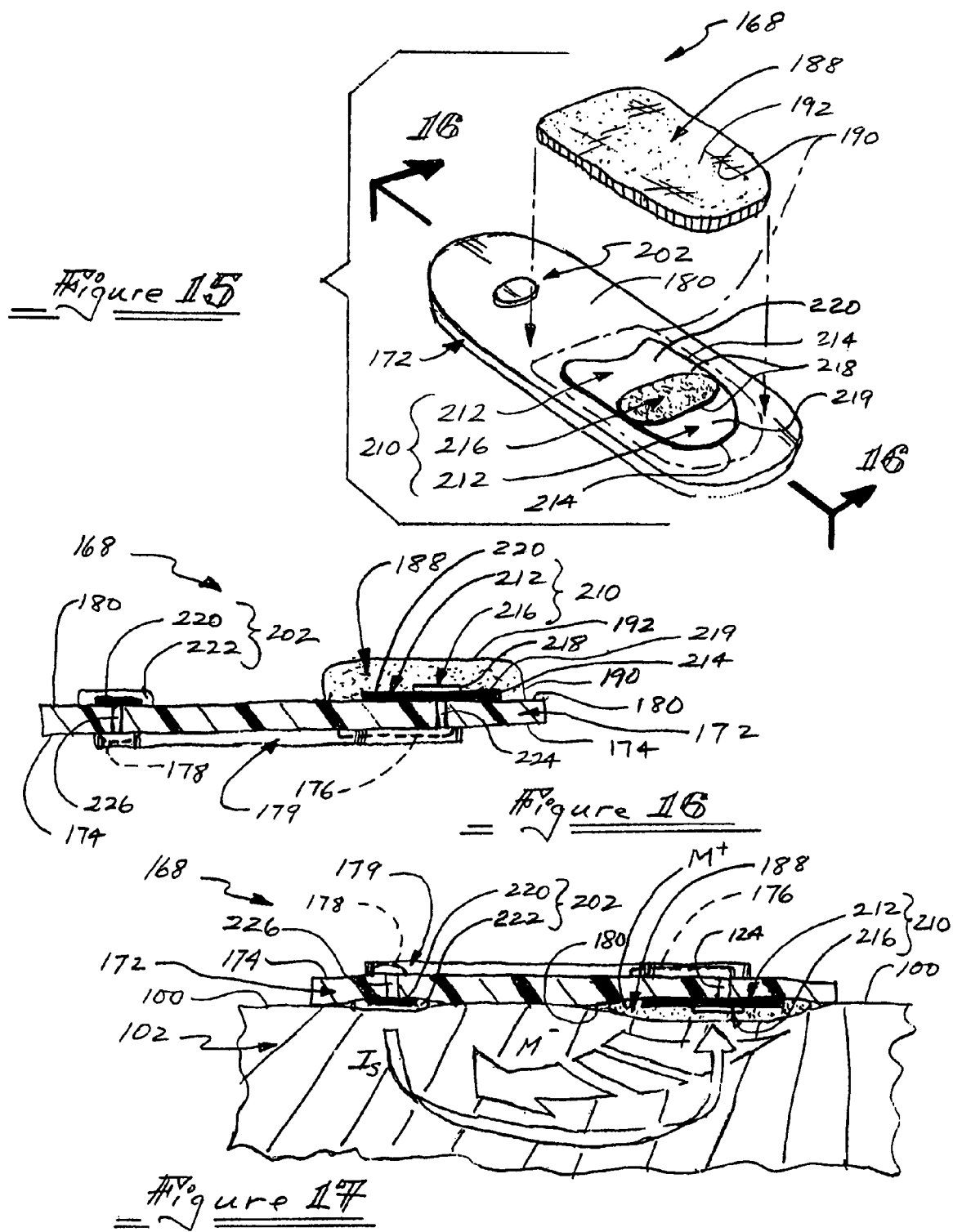

ACTIVE ELECTRODE FOR TRANSDERMAL MEDICAMENT ADMINISTRATION

RELATED APPLICATIONS

This application is related to U.S. Design patent application Ser. No. 29/261,600 that was filed on Jun. 16, 2006, and that issued on Sep. 2, 2008 as U.S. Design Pat. No. D576,282 for a design titled "Adhesive Transdermal Medicament Patch" and to U.S. patent application Ser. No. 11/701,749 that was filed on Feb. 2, 2007, and that published on Aug. 7, 2008 as United States Publication No. 2008-0188791, for an invention titled "Active Iontophoresis Delivery System".

BACKGROUND

1. Field of the Invention.

The invention disclosed herein relates to the transdermal administration of medicaments to human and animal subjects. More particularly, the present invention pertains to active iontophoretic delivery systems in which electrical contacts are applied to the surface of the skin of a subject for the purpose of delivering medicament through the surface of the skin into underlying tissues.

2. Background Art.

During active iontophoresis, direct electrical current is used to cause ions of a soluble medicament to move across the surface of the skin and to diffuse into underlying tissue. The surface of the skin is not broken by this administration of the medicament. When conducted within appropriate parameters, the sensations experienced by a subject during the delivery of the medicament in this manner are not unpleasant. Therefore, active iontophoresis presents an attractive alternative to hypodermic injections and to intravascular catheterization.

The direct current employed in active iontophoresis systems may be obtained from a variety of electrical power sources. These include electrical equipment that ultimately receives power from a wall socket, paired regions of contrasting galvanic materials that when coupled by a fluid medium produce minute electrical currents, and consumable and rechargeable batteries.

A flow of electrical current requires an uninterrupted, electrically-conductive pathway from the positive pole of a power source to the other, negative pole thereof. Living tissue is made up primarily of fluid and is, therefore, a conductor of electrical current. In an iontophoretic circuit, the opposite poles of a power source are electrically coupled to respective, separated contact locations on the skin of the subject. The difference in electrical potential created by the power source between those contact locations causes a movement of electrons and electrically charged molecules, or ions, through the tissue between the contact locations.

In an active iontophoretic delivery system, the polarity of the net overall electrical charge on dissolved molecules of a medicament determines the contact location on the skin at which a supply of the medicament of must be positioned. A positively charged medicament in a reservoir against the skin of a patient must be coupled to the positive pole of any power source that is to be used to administer the medicament iontophoretically. Correspondingly, a reservoir on the skin of a patient containing a negatively charged medicament must be coupled to the negative pole of such a power source. Examples of common iontophoretically administrable medicaments in each category of polarity are listed in the table below.

| Positive Polarity Medicaments | Negative Polarity Medicaments |
|---|---|
| Bupivacaine hydrochloride | Acetic acid |
| Calcium chloride | Betamethasone sodium phosphate |
| Lidocaine hydrochloride | Copper sulfate |
| Zinc chloride | Dexamethasone sodium phosphate |
| Lidocaine | Fentinol |
|  | Magnesium sulfate |
|  | Naproxen sodium |
|  | Sodium chloride |
|  | Sodium salicylate |

The medicament supply is housed in a fluid reservoir that is positioned electrically conductively engaging the skin of the subject at an anatomical location overlying the tissue to which medicament is to be administered. The medicament reservoir can take the form of a gel suspension of the medicament or of a pad of an absorbent matrix, such as gauze or cotton, which is saturated with fluid containing the medicament. In some instances the fluid containing the medicament is provided from the manufacturer in the absorbent matrix. More commonly, the fluid is added to the absorbent matrix by a medical practitioner at the time that the medicament is about to be administered to a subject.

An iontophoretic circuit for driving the medicament through the unbroken skin is established by coupling the appropriate pole of the power source through the medicament reservoir to the skin of the subject at the anatomical location at which the medicament is to be administered. Simultaneously, the other pole of the power source is coupled to an anatomical location on the skin of the subject that is distanced from the medicament reservoir. The coupling of each pole of the power source is effected by the electrical connection of each pole to a respective electrode. The electrode at the medicament reservoir is referred to as an active electrode; the electrode at the location on the skin distanced from the medicament reservoir is referred to as a return electrode.

The electrical potential that is imposed across the medicament reservoir of an iontophoretic circuit produces electrical current flow by causing electrolysis in some of the molecules of the water ($H_2O$) in the solution in the reservoir. In electrolysis, the positively-charged hydrogen ion ($H^+$) of a water molecule becomes separated from the negatively-charged hydroxyl radical ($HO^-$) of that same molecule. These ions and radicals then migrate in respective opposite directions through the solution in the medicament reservoir. The hydrogen ions ($H^+$) move toward the negative pole of the electrical potential being imposed on the solution, while the hydroxyl radicals ($HO^-$) move toward the positive pole.

The interaction of these migrating ions and radicals with themselves and with other of the chemicals in the solution has a tendency to change the initial hydrogen-ion concentration, or the pH, of the solution in the medicament reservoir. Instability in the pH of the solution in a medicament reservoir raises safety concerns. Any extreme that is allowed to develop in the pH of that solution over the course of therapy, gives rise to the possibility that the medicament reservoir in that condition altered pH condition will produce burns to the skin of the subject at the anatomical location on the skin that is in contact with the medicament reservoir.

The medicament reservoir with an associated active electrode may be conveniently retained against the skin by a first adhesive patch, while the return electrode may be retained against the skin at some distance from the medicament reservoir using a distinct second adhesive patch. Alternatively, the medicament reservoir with the associated active electrode, as well as the return electrode, may be carried on a single adhesive patch at, respective, electrically isolated locations.

The use of iontophoresis to administer medicaments to a subject is advantageous in several respects.

Medications delivered by an active iontophoretic system bypass the digestive system. This reduces digestive tract irritation. In many cases, medicaments administered orally are less potent than if administered transcutaneously. In compensation, it is often necessary in achieving a target effective dosage level to administer orally larger quantities of medicament than would be administered transcutaneously.

Active iontophoretic systems do not require intensive skin site sanitation to avoid infections. Patches and the other equipment used in active iontophoresis do not interact with bodily fluids and, accordingly, need not be disposed as hazardous biological materials following use. Being a noninvasive procedure, the administration of medicament using an active iontophoretic system does not cause tissue injury of the types observed with hypodermic injections and with intravenous catheterizations. Repeated needle punctures in a single anatomical region, or long term catheter residence, can adversely affect the health of surrounding tissue. Needle punctures and catheter implantations inherently involve the experience of some degree of pain. These unintended consequences of invasive transcutaneous medicament administration are particularly undesirable in an area of the body that, being already injured, is to be treated directly for that injury with a medicament. Such might be the case, for example, in the treatment of a strained muscle or tendon.

With some exceptions, no pharmacologically significant portion of a medicament delivered iontophoretically becomes systemically distributed. Rather, a medicament delivered iontophoretically remains localized in the tissue at the site of administration. This minimizes unwanted systemic side effects, reduces required dosages, and lightens the burdens imposed on the liver and kidneys in metabolizing the medicament.

The dosage of a medicament delivered iontophoretically is conveniently and accurately measured by monitoring the amount and the duration of the current flowing during the administration.

Finally, the successful operation of an active iontophoretic system is not reliant on the medical skills of nurses or doctors. Foregoing the involvement of such medical personnel in the administration of medicaments whenever appropriate favors the convenience of patients and reduces the costs associated with the delivery of such types of therapy.

SUMMARY OF THE INVENTION

The present invention promotes the wide use of active iontophoretic systems by providing improved components and combinations of components for active iontophoretic systems. The present invention thus improves the safety of patients and reduces the technical difficulty of related tasks that must by performed by medical personnel.

The teachings of the present invention enhance the reliability and the user friendliness of active iontophoretic systems and lead to reductions in the costs associated with the manufacture of such systems, as well as with the use of such systems to deliver medication.

The present invention has applicability in all types of active iontophoretic systems, those that involve a single, disposable, fully-integrated, adhesive transdermal medicament patch, and those that employ plural disposable adhesive patches in combination with reusable power sources and controls.

In one aspect of the present invention, an active electrode is provided for driving medicament from a medicament reservoir into the skin of a patient with a high degree of conductivity reliability.

In yet another aspect of the present invention, an active electrode is provided that has the capacity to stabilize pH-conditions in a medicament reservoir during any required period of therapy.

The present invention contemplates related methods of design and manufacture, as well as methods pertaining to the treatment of patient health problems.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

BRIEF DESCRIPTION OF THE DRAWINGS

The manner in which the above-recited and other advantages and objects of the invention are obtained will be understood by a more particular description of the invention rendered by reference to specific embodiments thereof that are illustrated in the appended drawings. These figures are intended to be illustrative, not limiting. Although the invention is generally described in the context of these embodiments, it should be understood that by so doing, no intention exists to limit the scope of the invention to those particular embodiments.

Understanding that these drawings depict only typical embodiments of the invention and are not therefore to be considered limiting of scope, the invention will be described and explained with additional specificity and detail through the use of the accompanying drawings in which:

FIG. 6 is an enlarged plan view of the active transdermal patch of FIG. 3 and a syringe containing a medicament solution that is being used to saturate a medicament matrix that is secured to the therapeutic face of the substrate of the patch;

FIG. 7A is a side elevation view of the active transdermal patch of FIG. 6 following the saturation of the medicament matrix of the patch with a medicament solution showing the release liner of the patch in a first stage of removal from the therapeutic face of the substrate of the patch;

FIG. 7B is a side elevation view like that shown in FIG. 7A with the release liner of FIG. 7A in a second and subsequent stage of removal;

FIG. 7C is a side elevation view like that shown in FIG. 7B with the release liner of FIG. 7B in a third and final stage of removal;

FIG. 15 is a partially-exploded perspective view of the active transdermal patch of FIG. 14;

FIG. 16 is a cross-sectional elevation view of the active transdermal patch of FIG. 15 in assembled condition taken along section line 16-16 shown therein;

FIG. 17 is a cross-sectional elevation view of the active transdermal patch of FIG. 16, but inverted and disposed against the skin of a patient, thereby to illustrate the movement of a medicament of positive polarity through the tissue of the patient.

DETAILED DESCRIPTION OF THE INVENTION

In the following description, for purpose of explanation, specific details are set forth in order to provide an understanding of the invention. Nonetheless, the present invention may be practiced without some or all of these details. The embodiments of the present invention, some of which are described below, may be incorporated into a number of elements of medical systems additional to the medical systems in which those embodiments are by way of necessity illustrated. Structures and devices shown in the figures illustrate merely exemplary embodiments of the present invention, thereby to facilitate discussion of teachings of the present invention. Thus, the details of the structures and devices shown in the figures are not included to facilitate an attempt to obscure broad teachings of present invention.

Connections between components illustrated in the figures are not limited to direct connections between those components. Rather, connections between such components may be modified, reformatted, or otherwise changed to include intermediary components without departing from the teachings of the present invention.

References in the specification to "one embodiment" or to "an embodiment" mean that a particular feature, structure, characteristic, or function described in connection with the embodiment being discussed is included in at least one embodiment of the present invention. Furthermore, the use of the phrase "in one embodiment" in various places throughout the specification is not necessarily a reference to any single embodiment of the present invention.

Figure 1:
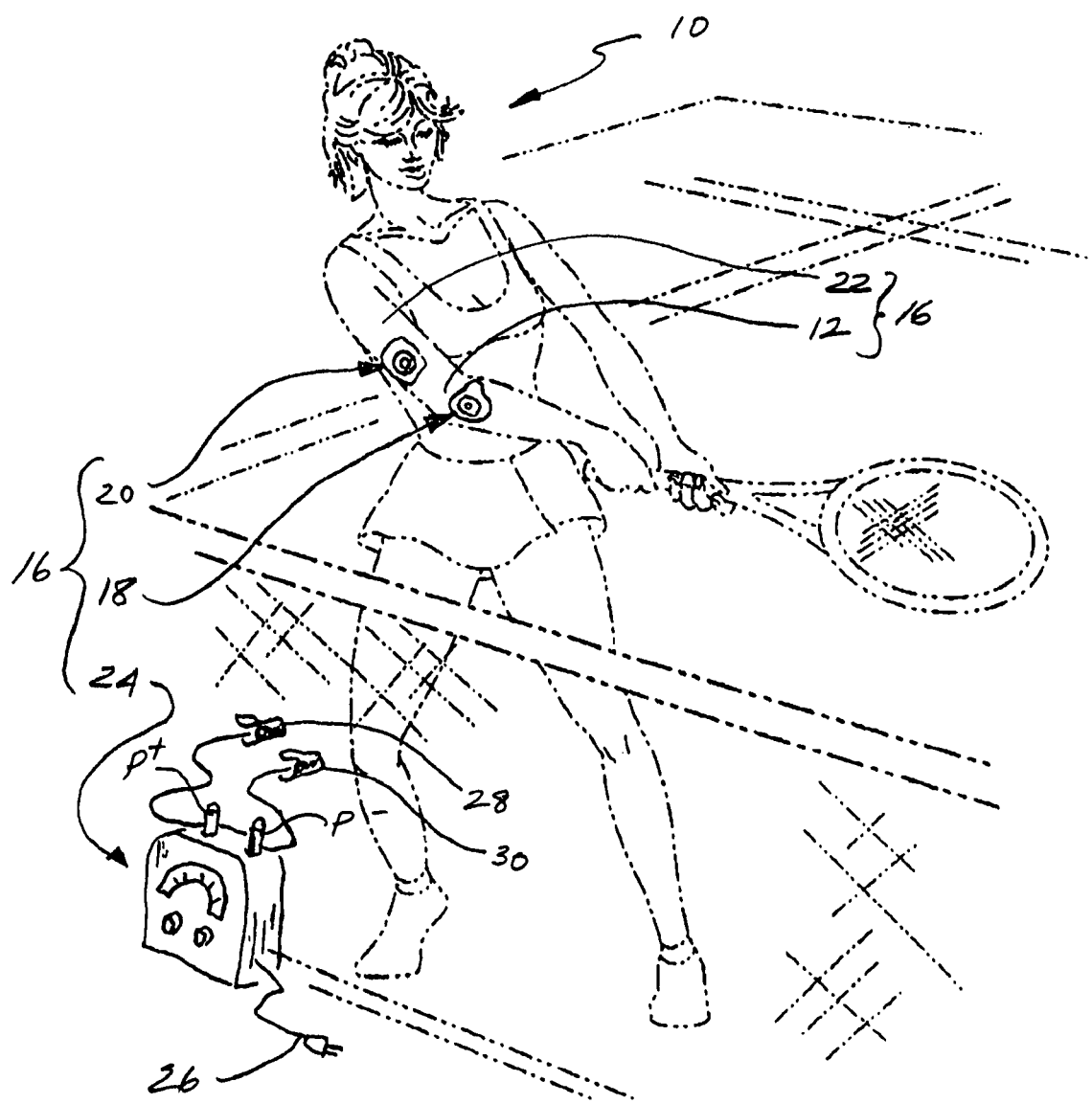
FIG. 1 is a perspective view of elements of a first embodiment of an active iontophoretic delivery system incorporating teachings of the present invention, some of which elements are depicted as being worn by a patient requiring the localized administration of a medicament.

FIG. 1 shows a patient 10 requiring the localized administration of a medicament to elbow 12 thereof. For that purpose, patient 10 is wearing on arm 16 thereof components of a first embodiment of an active iontophoretic delivery system 17 that incorporates teachings of the present invention. These components of delivery system 17 include an active transdermal medicament patch 18 worn on elbow 12 of patient 10 and an auxiliary patch 20 that is worn remote therefrom on upper arm 22. Medicament patch 18 and auxiliary patch 20 are removably adhered to the skin of patient 10 at these respective locations, and an iontophoretic current is made to flow therebetween through the skin and tissue of patient 10 by appropriately coupling to each of medicament patch 18 and auxiliary patch 20 an external power source 24 that is shown schematically in FIG. 1.

Power source 24 includes a wall cord 26, a positive pole $P^+$, an associated positive lead 28, a negative pole $P^-$, and an associated negative lead 30. In FIG. 1, positive lead 28 and negative lead 30 of power source 24 are disconnected temporarily from the other elements of delivery system 17, medicament patch 18 and auxiliary patch 20. Therefore, patient 10 is yet able to engage in vigorous physical activity as shown.

Medicament patch 18 carries a medicament reservoir filled with a medicament solution and an active electrode by which the electrical potential at an appropriate pole of power source 24 is communicated to and through the medicament reservoir to the skin of patient 10. If the medicament in the solution in the medicament reservoir on medicament patch 18 is positively charged, then positive pole $P^+$ of power source 24 is coupled electrically by way of positive lead 28 to medicament patch 18. If the medicament to be administered is negatively charged, then negative lead 30 is used to electrically couple negative pole $P^-$ of power source 24 to medicament patch 18. Auxiliary patch 20 carries a return electrode by which the electrical potential at the other pole of power source 24 is communicated to the skin of patient 10 at a contact location remote from the medicament reservoir on medicament patch 18.

FIGS. 2-5 taken together afford an overview of the structure of medicament patch 18.

Figure 2:
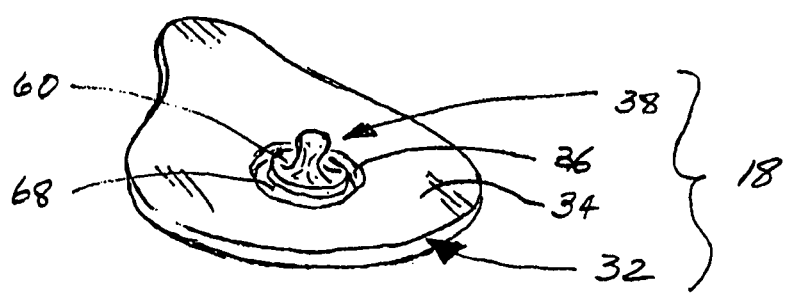
FIG. 2 is a perspective view of the active transdermal patch of the iontophoretic delivery system of FIG. 1 showing the upper face of the substrate of the patch that is visible when the patch is worn on the person of a patient.

FIG. 2 is a perspective view of medicament patch 18 showing the surface of medicament patch 18 that is exposed when medicament patch 18 is worn by patient 10 in the manner illustrated in FIG. 1. Thus, medicament patch 18 includes a flexible, planar biocompatible, non-electrically conductive, substrate 32 that has an upper face 34 that is visible when worn by patient 10. Formed though substrate 32 at a location convenient to the overall construction and functioning of medicament patch 18 is an electrical access aperture 36 through which projects an electrical contact 38 of the type to which electrical leads, such as positive lead 28 and negative lead 30 of power source 24, can be readily secured and nondestructively disengaged as needed. Electrical contact 38 is the feature of auxiliary patch 20 that enables the coupling of power source 24 to the active electrode carried by medicament patch 18.

Figure 3:
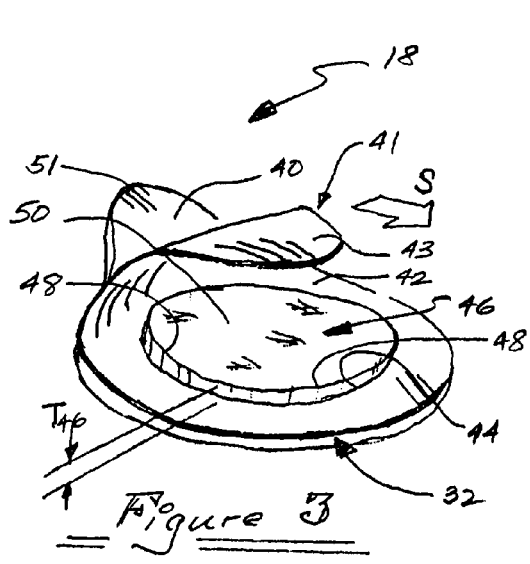
FIG. 3 is a perspective view of the active transdermal patch of FIG. 2 showing the therapeutic face of the substrate of the patch on the side thereof opposite that illustrated in FIG. 2 and depicting a release liner in the process of being peeled from the adhesive on the therapeutic face.

FIG. 3 is a perspective view of medicament patch 18 taken from the side of medicament patch 18 opposite from upper face 34 shown in FIG. 2. Revealed thusly is a therapeutic face 40 of substrate 32 that is intended to be disposed in contact with the skin of a patient, such as patient 10 in FIG. 1. Therapeutic face 40 is coated with a biocompatible adhesive to a sufficient extent as will enable therapeutic face 40 to be removably secured to the person of patient 10. Prior to the actual use of medicament patch 18, the adhesive on therapeutic face 40 is shielded by a removable release liner 41, which as suggested by arrow S in FIG. 3 is in the process of being peeled from therapeutic face 40. Release liner 41 has on the opposite sides thereof, respectively, first an exposed face 42 and second a contact face 43 that actually engages the adhesive on therapeutic face 40 of substrate 32.

Formed generally centrally through release liner 41 is a medicament matrix aperture 44. As shown in FIG. 3, medicament matrix aperture 44 is substantially filled by a generally planar medicament matrix 46 that exhibits a generally circular periphery 48. Medicament matrix 46 can take the form of a gel suspension of medicament or of an absorbent pad of gauze or cotton that is saturated at some time prior to use with a fluid solution containing medicament. When permeated by a medicament, medicament matrix 46 functions as the medicament reservoir of medicament patch 18.

The side of medicament matrix 46 visible in FIG. 3 forms a correspondingly circular skin contact surface 50 interior of periphery 48. Medicament matrix 46 projects through medicament matrix aperture 44 in such a manner that skin contact surface 50, while oriented generally parallel to the plane of release liner 41 and the plane of therapeutic face 40 of substrate 32, is separated from each by a distance that is approximately equal to the thickness $T_{46}$ of medicament matrix 46. By way of skin contact surface 50, medicament matrix 46 is intended to electrically conductively engage the skin of a patient, when therapeutic face 40 of substrate 32 is disposed against and removably adhered to the person of the patient.

Figure 4:
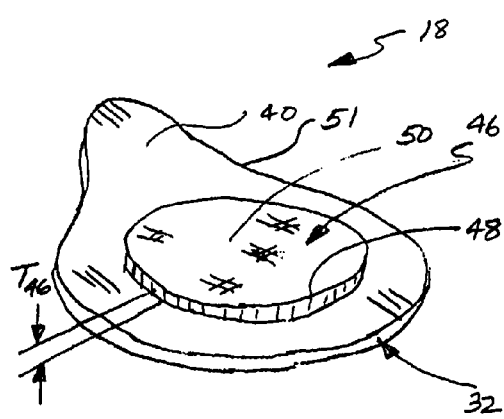
FIG. 4 is a perspective view of the therapeutic face of the active transdermal patch of FIG. 3 with the release liner illustrated in FIG. 3 fully removed.

FIG. 4 shows therapeutic face 40 of substrate 32 after the complete removal of release liner 41 therefrom. Medicament matrix 46 is positioned on therapeutic face 40 of substrate 18 with the periphery 48 of medicament matrix 46 interior of the periphery 51 of therapeutic face 40. Medicament matrix 46 is non-releasably retained there by the same adhesive that necessitates the use of release liner 41, or by any other appropriate arrangement. Medicament matrix 46 thus obscures a portion of therapeutic face 40 of substrate 32 that is concealed from view in FIG. 4. The balance of therapeutic face 40, the portion located between periphery 48 of medicament matrix 46 and periphery 51 of therapeutic face 40, is the portion of therapeutic face 40 that is exposed to view in FIG. 4.

Medicament matrix aperture 44 in release liner 41 and medicament matrix 46 on therapeutic face 40 of substrate 32 are closely similar in size and shape. As a result in FIG. 4, the edges of medicament matrix aperture 44 are in close proximity to periphery 48 of medicament matrix 46, when contact face 43 of release liner 41 is disposed covering the adhesive on the portion of therapeutic face 40 located between periphery 48 of medicament matrix 46 and periphery 51 of therapeutic face 40. Consequently, release liner 41 covers the entirety of that defined above as being the exposed portion of therapeutic face 40.

Medicament matrix aperture 44 in release liner 41 affords unimpeded access by medical personnel to the entirety of skin contact surface 50 of medicament matrix 46 prior to the removal of release liner 41 from therapeutic face 40. Additionally, the near congruency of periphery 48 of skin contact surface 50 of medicament matrix 46 with medicament matrix aperture 44 in release liner 41 advantageously allows release liner 41 to protect the adhesive on the exposed portion of therapeutic face 40 from any medicament solution that might overflow from medicament matrix 46 during the process of wetting medicament matrix 46 in anticipation of use.

Figure 5:
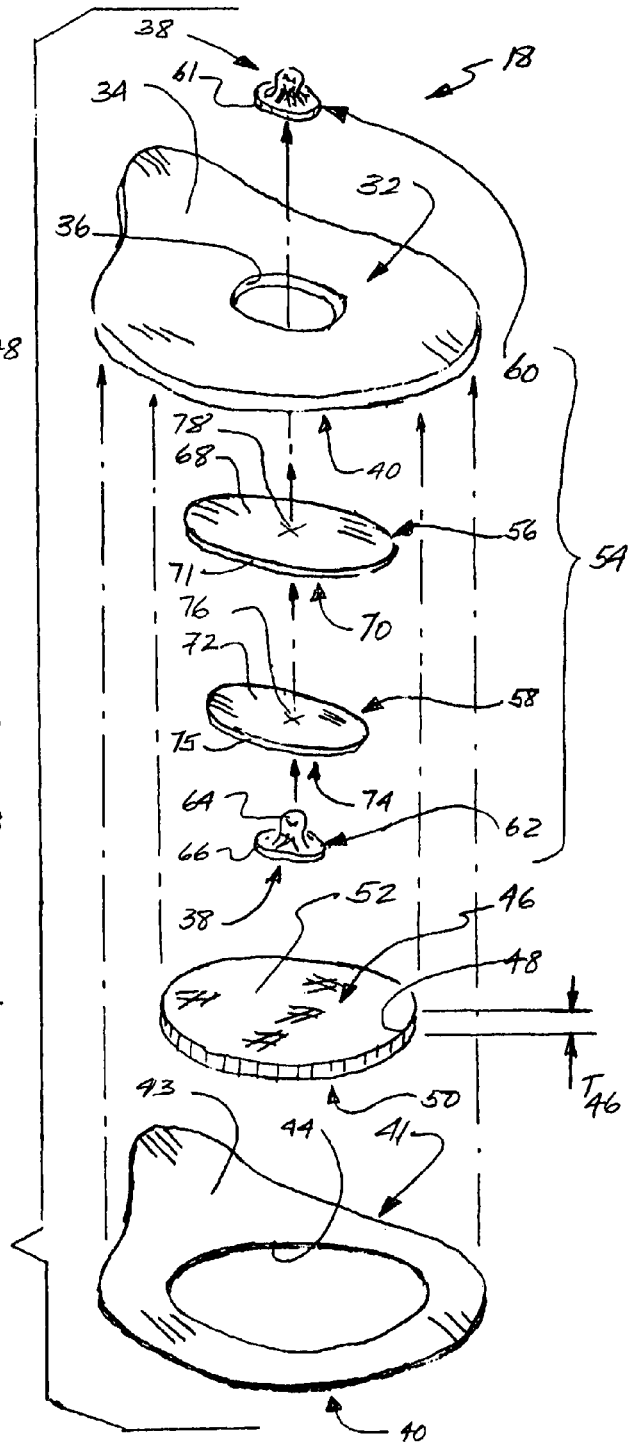
FIG. 5 is an exploded perspective view of the active transdermal patch of FIGS. 2-4 taken from the side of that patch shown in FIG. 2 and showing the upper face of the substrate of patch that is visible when the patch is worn on the person of a patient.

FIG. 5 is an exploded view of medicament patch 18 taken from the perspective of medicament patch 18 shown in FIG. 2. Shown accordingly in FIG. 5 are upper face 34 of substrate 32 and contact face 43 of release liner 41. Newly revealed on the side of medicament matrix 46 opposite from skin contact surface 50, which does not appear in FIG. 5, is a securement surface 52 of medicament matrix 46 by which medicament matrix 46 is retained on therapeutic face 40 of substrate 32.

Also revealed in FIG. 5 are the components of an active electrode 54. While not visible in the assembled condition of medicament patch 18 illustrated in FIGS. 3 and 4, in the assembled condition of medicament patch 18 active electrode 54 is sandwiched between medicament matrix 46 and the portion of therapeutic face 40 of substrate 32 concealed by medicament matrix 46. Active electrode 54 includes a backing layer 56, a pH-control layer 58, and electrical contact 38, which is itself a two-piece assembly. One component of electrical contact 38 is a hollow snap fitting 60 having a periphery 61 and an open end that is not visible in FIG. 5. In addition, electrical contact 38 includes a cooperating stud 62 that has a shaft 64 configured for press fit insertion through the open end of snap fitting 60 and a generally planar flange 66 secured to an end of shaft 64.

The side of backing layer 56 shown in FIG. 5 functions as a securement surface 68 of backing layer 56 by which backing layer 56 engages and may be attached to therapeutic face 40 of substrate 32. In so doing, backing layer 56 is positioned across electrical access aperture 36. Thus, in FIG. 2, it is securement surface 68 of backing layer 56 that is visible from upper face 34 of substrate 32 through electrical access aperture 34 between substrate 32 and periphery 61 of snap fitting 60. The opposite side of backing layer 56, which is not shown in FIG. 5, defines a driving face 70 of backing layer 56 that at least in part contacts securement surface 52 of medicament matrix 46 in the assembled condition of medicament patch 18 shown in FIGS. 2-4. Backing layer 56 has a periphery 71 that appears to be circular, but that may assume many other configurations.

Correspondingly, the side of pH-control layer 58 presented to view in FIG. 5 is a securement surface 72 of pH-control layer 58. All or some of securement surface 72 abuts a portion only of driving face 70 of backing layer 56 in the assembled condition of active electrode 54. Any portion of securement surface 72 of pH-control layer 58 that does not abut driving face 70 of backing layer 56 eventually becomes attached to therapeutic face 40 of substrate 32 in the assembled condition of medicament patch 18 presented in FIGS. 2-4. The opposite side of pH-control layer 58, which is also not visible in FIG. 5, defines a driving face 74 of pH-control layer 58. Driving face 74 of backing layer 56 engages securement surface 52 of medicament matrix 46 in the assembled condition of medicament patch 18. Finally, pH-control layer 58 has a periphery 75 that is circular, seemingly in echo of periphery 71 of backing layer 56. Nonetheless, periphery 75 of pH-control layer 58 may assume many other configurations and need not echo the configuration of periphery 71 of backing layer 56 in any manner whatsoever.

One method for making a medicament patch, such as medicament patch 18, will be described. In that method, the manufacture of active electrode 54 precedes the assembly of active electrode 54 with the other elements of medicament patch 18 shown in FIG. 5.

In active electrode 54, pH-control layer 56 is made of an electrically conductive material that is, under conditions of iontophoretic current flow through medicament patch 18, capable of moderating changes in the hydrogen-ion concentration, or the pH, in medicament matrix 46. Moderating changes in the hydrogen-ion concentration in medicament matrix 46 is equivalent to moderating the hydroxyl-radical concentration in medicament matrix 46. Iontophoretic current arises, when medicament patch 18 is adhered to the skin of a patient, and an electrical potential is imposed between active electrode 54 and the skin of the patient at a contact location remote from medicament matrix 46

The ability of pH-control layer 58 to moderate changes in the hydrogen-ion concentration in medicament matrix 46 can be achieved in a number of different ways through the use of various materials to construct pH-control layer 58.

For example, the material of which pH-control layer 58 is formed can be a material that is capable of precluding the electrolysis of the water ($H_2O$) in medicament matrix 46 by competing to be electrolyzed instead of that water ($H_2O$) during iontophoretic current flow. Examples of such materials include a mixture of silver (Ag) and silver-chloride (AgCl) or a mixture of potassium (K) and potassium-chloride (KCl). These materials electrolyze before water and when so doing produce constituent chemical components that do not change the pH in medicament matrix 46.

Alternatively, the material of which pH-control layer 58 is formed can be a material that is capable of neutralizing the chemical products created by the electrolysis of water ($H_2O$) in medicament matrix 46 during iontophoretic current flow. An example of such a material is potassium phosphate ($K_3PO_4$).

Backing layer 56 is made from a film of a more common electrically conductive material, such as carbon (C), copper (Cu), aluminum (Al), or rubberized carbon. Backing layer 56 has a thickness in a range from about 1.0 millimeter to about 5.0 millimeters. The material of pH-control layer 58 is applied to driving face 70 of backing layer 56, by printing or by deposition through a mask shaped to correspond to that intended in pH-control layer 58. Either before or following that deposition, the electrically conductive film from which backing layer 56 is fabricated is cut into the shape desired in backing layer 56. According to teachings of the present invention, pH-control layer 58 covers less than all of driving face 70 of backing layer 56. As a result, all of pH-control layer 58, but only the portion of driving face 70 of backing layer 56 that is free of pH-control layer 58, is able to electrically engage securement surface 68 of medicament matrix 46, when active electrode 54 is assembled with the other elements of medicament patch 18.

To complete the manufacture of electrical contact 38, the components of electrical contact 38 are fitted together with pH-control layer 58 and backing layer 56 sandwiched therebetween.

The free end of shaft 64 of stud 62 is forced through pH-control layer 58 at a generally central location 76 and then through backing layer 56 at a generally central location 78. Alternatively, apertures through which to advance shaft 64 may be formed in advance through an appropriate location in one or both of pH-control layer 58 and backing layer 56. Finally, the free end of shaft 64 of stud 62 is inserted into the open end of snap fitting 60. By press fitting or by other appropriate arrangements, stud 62 becomes permanently secured thereto. Backing layer 56 and pH-control layer 58 are thereby clamped between snap fitting 60 and flange 66 of stud 62, and the assembly of active electrode 54 is complete.

Snap fitting 60 is made of an electrically conductive material. Therefore, once the assembly of active electrode 54 is complete, snap fitting 60 is correspondingly electrically coupled to securement surface 68 of backing layer 56. As mentioned earlier, backing layer 56 and pH-control layer 58 are both made of electrically conductive materials. Accordingly, in the assembled condition of active electrode 54, snap fitting 60 becomes electrically coupled to the entirety of backing layer 56, including in particular driving face 70 thereof. As driving face 70 of backing layer 56 abuts securement surface 72 of pH-control layer 58, snap fitting 60 is also electrically coupled to the entirety pH-control layer 58, including in particular driving face 74 thereof. Active electrode 54 is thus a single, electrically conductive structure that communicates to securement surface 52 of medicament matrix 46 the electrical potential that is applied to snap fitting 60 from power source 24 shown in FIG. 1. The electrical potential may be, either a positive electrical polarity that is provided through positive lead 28, or a negative electrical polarity that is provided through negative lead 30.

The types of material that may be used as stud 62 warrant discussion.

Stud 62 can be made of an electrically conductive material, possibly even the same type of electrically conductive material as that from which snap fitting 60 is manufactured. Then, with shaft 64 of stud 62 engaged in snap fitting 60 in the assembled condition of electrical contact 38, any electrical potential applied to snap fitting 60 from power source 24 will be directly communicated to the entirety of electrical contact 38, including in particular to flange 66 of stud 62. Like driving face 74 of pH-control layer 58 in the assembled condition of medicament patch 18, flange 66 of stud 62 directly engages securement surface 52 of medicament matrix 46.

In the assembled condition of medicament patch 18, the presence of flange 66 on driving face 74 of pH-control layer 58 impedes the migration of the chemical constituents of pH-control layer 58 into the region of medicament matrix 46 that is located on the opposite side of flange 66 from pH-control layer 58. These are the material that are intended to moderate changes in the hydrogen-ion concentration, or the pH, in medicament matrix 46 during iontophoretic current flow. Regions of medicament matrix 46 are thus eclipsed by flange 66 from the full beneficial pH moderating effects that are intended to be exercised upon medicament matrix 46 by pH-control layer 58. As a result, these eclipsed regions of medicament matrix 46 are more likely to become caustic during the course of iontophoretic current flow than is the balance of medicament matrix 46. The regions of medicament matrix 46 thusly eclipsed by flange 66 are inclined to exhibit pH instability, and the portion of skin contact surface 50 of medicament matrix 46 adjacent to those regions is correspondingly inclined to cause injury to the skin against which medicament patch 18 is disposed.

This problem of localized regions of pH instability in skin contact surface 50 of medicament matrix 46 is exacerbated when stud 62 of electrical contact 38 is constructed from an electrically conductive material.

Then, the electrical potential applied to snap fitting 60 from power source 24 is directly communicated to flange 66, which is in turn in an abutting relationship to securement surface 52 of medicament matrix 46. The electric field associated with flange 66 is imposed on the region of medicament matrix 46 opposite thereto with an intensity that is greater than the intensity imposed on medicament matrix 46 by active electrode 54 as a whole. This unevenness in the intensity of the electric field throughout medicament matrix 46 causes a corresponding disparity in the rate of electrolysis of the water ($H_2O$) at locations in medicament matrix 46. In particular, the rate of electrolysis of water ($H_2O$) is accelerated in the region of medicament matrix 46 that is directly opposite from flange 66 of electrical contact 38. This is, however, the very region of medicament matrix 46 in which pH instability is most likely, due to the eclipsing of driving face 74 of pH-control layer 58 by flange 66 in the manner discussed above. To ameliorate these conditions, flange 66, or at least the surface thereof that engages securement surface 52 of medicament matrix 46, may be coated with a material of the types disclosed above by which pH-control layer 58 is rendered capable of moderating changes in the hydrogen-ion concentration in medicament matrix 46.

According to another aspect of the present invention, in one embodiment of an active electrode, such as active electrode 54, stud 62, or at least flange 66 thereof, is comprised of a material that is electrically insulative. Then coating flange 66 with a material that moderates changes in the hydrogen-ion concentration in medicament matrix 46 may not be warranted. When stud 62, or at least flange 66 thereof, is comprised of a material that is electrically insulative, the electrical potential applied to snap fitting 60 is not communicated to flange 66, and no unusual acceleration of the electrolysis of water ($H_2O$) should then result in regions of medicament matrix 46 that are directly opposite from flange 66.

An assembled active electrode 54 is combined in the following manner with the other elements of medicament patch 18 shown in FIG. 5.

Sheeting of a flexible biocompatible material is cut into the shape of substrate 32, electrical access aperture 36 is formed therethrough, and an adhesive is applied to the side that is intended to function as therapeutic face 40. These steps can be performed in any order that is most convenient and economical. Active electrode 54 is then disposed against the adhesive on therapeutic face 40 of substrate 32 in such a manner that snap fitting 60 of electrical contact 38 projects through electrical access aperture 36 in substrate 32 in the manner shown in FIG. 2.

An absorbent material, such as gauze or cotton, is cut or otherwise configured into the shape desired in medicament matrix 46. Medicament matrix 46 can alternatively be formed from a medical grade gel, such as a hydro gel, that is saturated with medicament. In any case, medicament matrix 46 is then attached by securement surface 52 thereof to therapeutic face 40 of substrate 32, by the adhesive on therapeutic face 40, or through any other arrangement. In the process, that medicament matrix 46 must completely cover active electrode 54.

The portion of therapeutic face 40 thereby obscured by medicament matrix 46 defines a concealed portion of therapeutic face 40, while the portion of therapeutic face 40 other than the concealed portion thereof defines an exposed portion of therapeutic face 40. It should be noted that the portion of therapeutic face 40 contacted by active electrode 54 is also covered, and therefor obscured, by medicament matrix 46. Therefore, the portions of therapeutic face 40 contacted by active electrode 54 directly, as well as that contacted by medicament matrix 46 directly are included in the concealed portion of therapeutic face 40 as defined above.

Finally, thin nonabsorbent sheeting of a flexible biocompatible material is cut into the shape of release liner 41, medicament matrix aperture 44 is formed therethrough, and contact face 43 of release liner 41 is disposed on the adhesive on the exposed portion of therapeutic face 40 with medicament matrix 46 projecting in close conformity through medicament matrix aperture 44. To the extent practicably, no portion of medicament matrix 46 should be obscured by release liner 41. As a result, the full extent of skin contact surface 50 of medicament matrix 46 will remain accessible to medical personnel, even while release liner 41 remains in covering engagement with therapeutic face 40. The portions of contact face 43 of release liner 41 immediately adjacent to medicament matrix aperture 44 are then, temporarily adhered to the adhesive on therapeutic face 40 immediately adjacent to periphery 48 of medicament matrix 46. In this manner, a fluid tight seal is effected on behalf to the entirety of the exposed portion of therapeutic face 40 between from any fluid in or intended for medicament matrix 46.

The benefit of this relative arrangement among the components of medicament patch 18 is illustrated and will be discussed in relation to FIGS. 6 and 7A-7C.

FIG. 6 is a plan view of the side of medicament patch 18 from which medicament matrix 46 is visible projecting through medicament matrix aperture 44 in release liner 41. Also shown is a syringe 80 containing a medicament solution 82 that is being used to saturate medicament matrix 46 in anticipation of the use of medicament patch 18. Drops of medicament solution 82 are deposited on skin contact surface 50 of medicament matrix 46 as suggested by arrow X and permitted to soak thereinto.

As this process progresses, a saturated portion 84 that is stippled in FIG. 6 develops in medicament matrix 46 and grows laterally as additional drops of medicament solution 82 are added to medicament matrix 46. Saturated portion 84 of medicament matrix 46 is visually distinguishable by a medical practitioner from the unsaturated portions of medicament matrix 46. As no portion of medicament matrix 46 is covered by release liner 41, a medical practitioner is thereby able to observe the enlargement of saturated portion 84 of medicament matrix 46 as drops of medicament solution 82 are added thereto, eventually verifying by visual inspection that the entirety of medicament matrix 46 has been adequately wetted It is not uncommon that medicament matrix 46 may become locally oversaturated in some areas during this wetting process. Then, medicament solution 82 may overflow medicament matrix 46. This overflow of medicament solution 82 does not come into contact with the adhesive on substrate 32. Rather the overflow is deposited on exposed face 42 of release liner 41.

Such a situation is illustrated in FIG. 6. There the lateral expansion of saturated portion 84 is shown to have reached a first section 86 of periphery 48 and a second section 88 of periphery 48 in advance of the complete wetting of medicament matrix 46 with medicament solution 82. Fluid pressure behind first section 86 of periphery 48 has caused medicament solution 82 to be discharged onto exposed face 42 of release liner 41, forming there a first overflow 90 of medicament solution 82. So long as medicament solution 82 continues to be added to medicament matrix 46, first overflow 90 will expand along exposed face 42 of release liner 41 away from periphery 48 of medicament matrix 46 in a manner suggested by arrows $Y_{90}$. Similarly, at second section 88 of periphery 48 of medicament matrix 46, a second overflow 92 of medicament solution 82 from medicament matrix 46 has come to form on exposed face 42 of release liner 41. So long as medicament solution 82 continues to be added to medicament matrix 46, second overflow 92 will expand along exposed face 42 of release liner 41 away from periphery 48 of medicament matrix 46 in a manner suggested by arrows $Y_{92}$.

Frequently during the process of wetting medicament matrix 46 with medicament solution 82, droplets of medicament solution 82 are inadvertently deposited on medicament patch 18 remote from medicament matrix 46. Such droplets are precluded from contacting the adhesive on substrate 32 by release liner 41. In FIG. 6, such droplets 94 of medicament solution 82 are shown to have come to rest on exposed face 42 of release liner 41.

In the alternative to using a syringe of medicament solution, the wetting of a medicament matrix, such as medicament matrix 46, can be accomplished through the bursting onto the medicament matrix of a capsule or blister of medicament solution that constitutes an integral component of the medicament patch, an element of the packaging for the medicament patch, or a article distinct from both.

A release liner configured in the manner of release liner 41 and assembled in the manner illustrated in FIG. 6 with medicament matrix aperture 44 closely surrounding periphery 48 of medicament matrix 46, prevents wetting of the portion of therapeutic face 40 not engaged by medicament matrix 46. This preserves the capacity of the exposed adhesive on substrate 32 to reliably adhere to the skin of a patient and maintains the capacity of that adhesive to electrically insulate medicament matrix 46 in the plane of the skin of a patient, once medicament patch 18 is adhered to the person of the patient. Were that adhesive to become wetted, with medicament solution 82 before being used to adhere medicament patch 18 to the skin, then the electrically conductive pathways arising in trails of medicament solution 82 between medicament patch 18 and the skin would render active electrode 54 susceptible to being shorted along the surface of the skin to the return electrode carried on auxiliary patch 20 shown in FIG. 1.

These teachings of the present invention have equal applicability to the design and construction of a transdermal medicament patch that, lacking any features by which to drive medicament into the skin electrically, is not active in the sense intended for that expression herein. Typically, such a non-active transdermal medicament patch relies merely on maintaining a medicament on the patch in long term contact with the skin, thereby to allow the medicament to diffuse across the surface of the skin and into underlying tissues at whatever rate results due to the nature of the medicament being used, the quality of the contact effected, and the condition of the surface of skin at the location of the contact. Nonetheless, any non-active medicament patch that administers a medicament in solution, whether placed on that patch by the manufacturer or by medical personnel, can benefit from a release liner configured with a medicament matrix aperture in the manner of release liner 41 and assembled in the manner illustrated in FIG. 6 with the medicament matrix aperture closely surrounding the periphery of a medicament matrix carried on the substrate of the medicament patch.

FIGS. 7A-7B are a sequence of diagrams depicting in a side elevation view of medicament patch 18 of FIG. 6 the effects produced on first overflow 90, second overflow 92, and droplets 94 of medicament solution 82 by of the removal of release liner 41 from medicament patch 18 in the manner suggested by arrow S in FIG. 3.

FIG. 7A shows release liner 41 in a first stage of removal from medicament patch 18 in which an edge 96 of release liner 41 to the left in FIG. 7A has been separated from the adhesive there beneath on therapeutic face 40 of substrate 32. As suggested by arrow A in FIG. 7A, edge 96 of release liner 41 continues from the state thereof shown to be raised upwardly, away from an increasing larger fraction of the exposed portion of therapeutic face 40 of substrate 32.

In FIG. 7B, release liner 41 is shown in a subsequent second or intermediate stage of removal from medicament patch 18. The lifting of edge 96 of release liner 41 in the manner indicated by arrow A in FIG. 7A has begun to free from coverage by release liner 41 an even larger fraction of the adhesive on the exposed portion of therapeutic face 40 of substrate 32. In FIG. 7B, that newly uncovered area of the adhesive on therapeutic face 40 extends along therapeutic face 40 to first section 86 of periphery 48 of medicament matrix 46. As a result of the increasing slope of exposed face 42 of release liner 41, droplets 94 and first overflow 90 can be seen to have begun to flow away from edge 96 of release liner 41 toward medicament matrix 46 as suggested by arrows $Z_1$. Consequently, the medicament solution in first overflow 90 in particular is urged to flow around or back into medicament matrix 46, and saturated portion 84 of medicament matrix 46 can be seen to have grown to encompass more of the entirety of periphery 48 of medicament matrix 46 than was the case in FIG. 7A. A portion of saturated portion 84 of medicament matrix 46 is visible in FIG. 7B below contact face 43 of release liner 41. As indicated by arrow B, the removal of release liner 41 continues from the state thereof shown to be raised upwardly, away from the adhesive on therapeutic face 40 of substrate 32.

In a final stage of the removal of release liner 41 from medicament patch 18 depicted in FIG. 7C, edge 96 of release liner 41 has disappeared entirely out of view. Medicament solution 82 in droplets 94 and in first overflow 90 has been borne back into medicament matrix 46 or entirely away from medicament patch 18. Saturated portion 84 medicament matrix 46 has grown to comprehend the entirety of medicament matrix 46. As suggested by arrows $Z_2$, second overflow 92 is being induced by the increasing slope of release liner 41 in the vicinity thereof to fall over an edge 98 of release liner 41 on the opposite side of release liner 41 from edge 96. As indicated by arrow C, the removal of release liner 41 continues from the state thereof shown to be removed laterally from substrate 32 until medicament patch 18 is in a condition that can be retained on the person of a patient. Then therapeutic face 40 of substrate 32 will be adhered to the person of the patient with fully wetted skin contact surface 50 of medicament matrix 46 electrically engaging the skin of the patient.

Figure 8A:
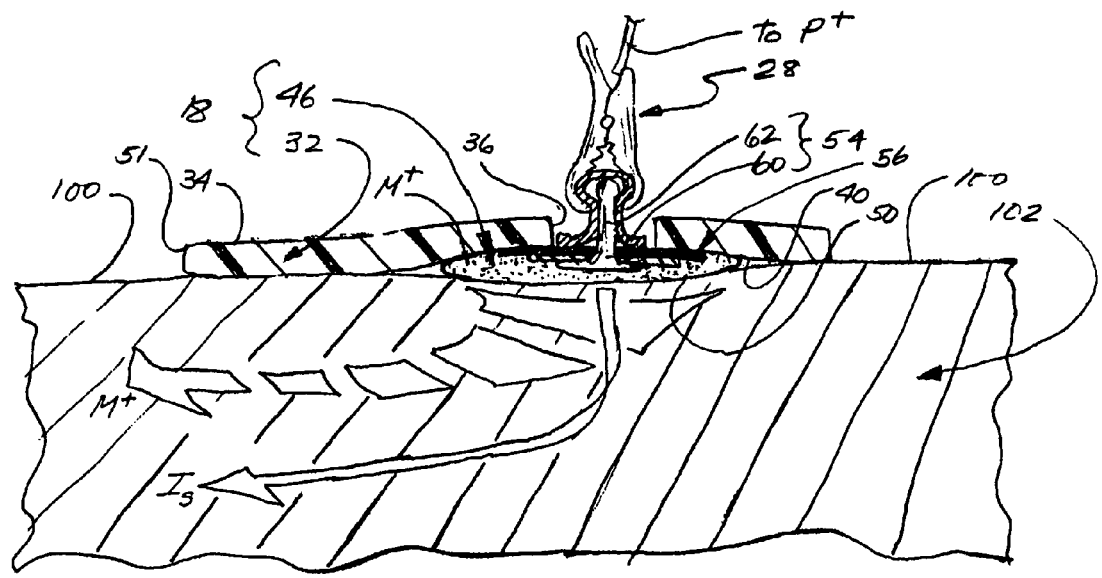
FIG. 8A is cross-sectional elevation view of the active transdermal patch of FIG. 6 taken along section line 8A-8A shown therein, but inverted and disposed against the skin of a patient, thereby to illustrate the movement of a medicament of positive polarity through the tissue of the patient.
Figure 8B:
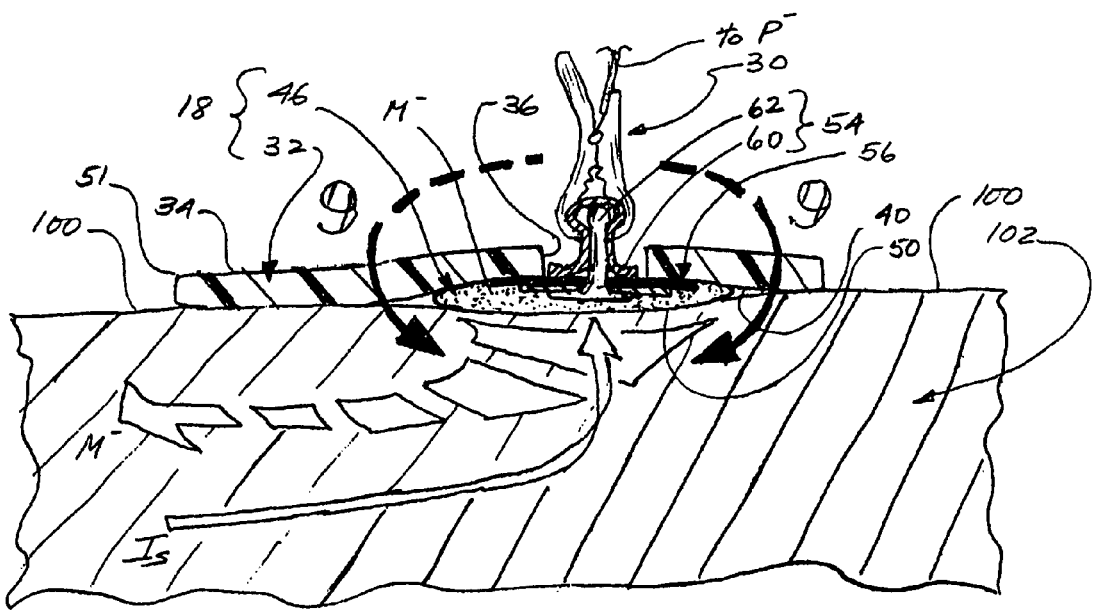
FIG. 8B is a diagram like that of FIG. 8A, illustrating the movement of a medicament of negative polarity through the tissue of a patient.

Such is the situation depicted in cross section in FIGS. 8A and 8B, which are related diagrams that compare the movement of molecules of medicaments of differing polarities through the tissue of a wearer of medicament patch 18, and the altered electrical interconnections required among selected element of delivery system 17 to produce those respective movements.

FIG. 8A illustrates the movement of molecules of a positive medicament $M^+$ that is contained in medicament matrix 46 of medicament patch 18. Therapeutic face 40 of substrate 32 is shown as being disposed against the surface 100 of skin 102. Then skin contact surface 50 of medicament matrix 46 electrically conductively engages surface 100 of skin 102. The positive pole $P^+$ of power source 24 of FIG. 1 is coupled by way of positive lead 28 to snap fitting 60 of active electrode 54 and therefrom through medicament matrix 46 of medicament patch 18 to skin 102 at a first contact location thereon. Although not shown in FIG. 8A, the negative pole $P^-$ of power source 24 is correspondingly coupled to auxiliary patch 20 and through the return electrode carried thereon to skin 102 at a second contact location that is remote from medicament matrix 46 and medicament patch 18. Aside from the conductivity of skin 102, the first contact location and the second contact location are electrically isolated from each other. The electromotive differential thusly applied to skin 102 between medicament matrix 46 and auxiliary patch 20 induces molecules of positive medicament $M^+$ to move as positive ions out of medicament matrix 46, toward skin 102, across the unbroken surface 100 of skin 102, and through skin 102 in the direction of auxiliary patch 20. This movement is indicated in FIG. 8A by a dashed arrow labeled $M^+$.

In electrical circuits, the flow of current is conventionally indicated as a flow of electrons through the circuit from the positive to the negative pole of the power source employed therewith. Therefore, in FIG. 8A, a skin current $I_S$ is schematically indicated by a solid arrow to flow through skin 102 from medicament matrix 46, which is associated with positive pole $P^+$ of power source 44 in FIG. 1, to auxiliary patch 20, which is associated with negative pole $P^-$ of power source 24. In the use of medicament patch 18 to administer a positive medicament $M^+$, the direction of movement of molecules of positive medicament $M^+$ through skin 102 thus coincides with the direction of electrical current $I_S$.

In FIG. 8B, transcutaneous administration is intended of molecules of a negative medicament $M^-$ that is contained in medicament matrix 46 of medicament patch 18. Under such conditions, the electrical interconnections required to be made among the components of delivery system 17 must be altered from those shown and discussed in relation to FIG. 8A.

Accordingly, in FIG. 8B therapeutic face 40 of substrate 32 is shown as being disposed against surface 100 of skin 102. Then skin contact surface 50 of medicament matrix 46 electrically conductively engages surface 100 of skin 102. The negative pole $P^-$ of power source 24 of FIG. 1 is coupled by way of negative lead 30 to snap fitting 60 of active electrode 54 and therefrom through medicament matrix 46 of medicament patch 18 to skin 102 at a first contact location thereon. Although not shown in FIG. 8A, the positive pole $P^+$ of power source 24 is correspondingly coupled to auxiliary patch 20 and through the return electrode carried thereon to skin 102 at a second contact location that is remote from medicament matrix 46 and medicament patch 18. Aside from the conductivity of skin 102, the first contact location and the second contact location are electrically isolated from each other. The electromotive differential thusly applied to skin 102 between medicament matrix 46 and auxiliary patch 20 induces molecules of negative medicament $M^-$ to move as negative ions out of medicament matrix 46, toward skin 102, across the unbroken surface 100 of skin 102, and through skin 102 in the direction of auxiliary patch 20. This movement is indicated in FIG. 8B by a dashed arrow labeled $M^-$.

As mentioned earlier, the flow of current in an electrical circuit is conventionally indicated as a flow of electrons through the circuit from the positive to the negative pole of the power source employed therewith. In FIG. 8B, a skin current $I_S$ is schematically indicated by a solid arrow to flow through skin 102 toward medicament matrix 46, which is associated with negative pole $P^-$ of power source 24 in FIG. 1, from auxiliary patch 20, which is associated with positive pole $P^+$ of power source 24. In the use of medicament patch 18 to administer negative medicament $M^-$, the movement of molecules of negative medicament $M^-$ through skin 102 is in a direction that is opposite from that of electrical current $I_S$.

For convenience and consistency in discussing the various embodiments of the present invention that are to be disclosed subsequently, the convention will be uniformly observed that a negative medicament $M^-$ is to be administered. Nonetheless, this is not an indication that the teachings of the present invention as manifested in the various embodiments of the present invention disclosed herein have relevance exclusively to the administration of a negative medicament $M^-$, as the present invention has applicability with equal efficacy to the administration of a positive medicament $M^+$.

Figure 9:
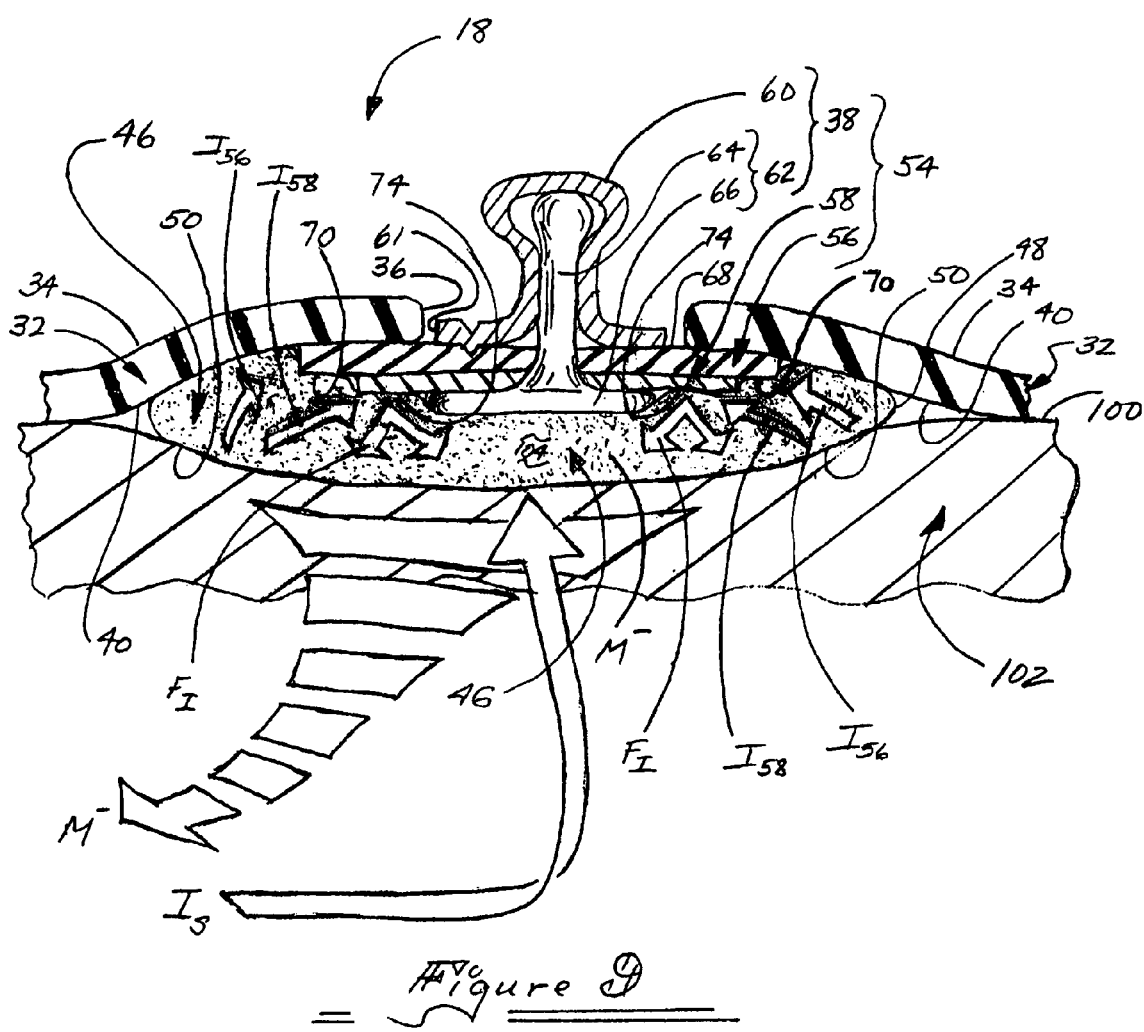
FIG. 9 is an enlarged cross-sectional detail of the active electrode of the active transdermal patch of FIG. 8B.

FIG. 9 is an enlarged cross-sectional detail of the portion of medicament patch 18 of FIG. 8B that includes active electrode 54. As a result, FIG. 9 depicts in edge view both upper face 34 and therapeutic face 40 of substrate 32, as well as the interaction therewith and among the components of active electrode 54 shown in FIG. 5.

Therapeutic face 40 of substrate 32 is shown disposed against surface 100 of skin 102 of a patient, whereby skin contact surface 50 of medicament matrix 46 simultaneously electrically engages surface 100 of skin 102. As medicament matrix 46 is saturated by a negative medicament $M^-$, active electrode 54 is coupled to the negative pole $P^-$ of power source 24 of delivery system 17 from FIG. 1, although in contrast to FIG. 8B indications of this arrangement are not included in FIG. 9. It is, however, indicated diagrammatically in FIG. 9 by a dashed arrow labeled $M^-$ that this arrangement enables active electrode 54 to drive negative medicament $M^-$ from medicament matrix 46 and through skin 102. Correspondingly, a skin current $I_S$ is schematically indicated by a solid arrow in FIG. 9 to flow in the opposite direction through skin 102 toward medicament matrix 46.

Active electrode 54 is shown as being sandwiched between medicament matrix 46 and therapeutic face 40 of substrate 32 interior of periphery 48 of medicament matrix 46. Snap fitting 60 of electrical contact 38 of active electrode 54 projects through electrical access aperture 36 in substrate 32 and away from skin 102, thereby being easily accessible for electrical connection to a lead from a source of electrical power. To maintain this desired position of active electrode 54 relative to the other elements of medicament patch 18, securement surface 68 of backing layer 56 of active electrode 54 is adhered to therapeutic face 40 of substrate 32 in the vicinity of electrical access aperture 36. Medicament matrix 46 is then adhered to at least a portion of therapeutic face 40 of substrate 32 surrounding active electrode 54. Active electrode 54 is thereby precluded from effecting direct electrical contact with surface 100 of skin 102 against which medicament patch 18 is disposed.

Among the elements of active electrode 54, pH-control layer 58 can be seen carried on driving face 70 of backing layer 56. As pH-control layer 58 covers less than all of driving face 70, the portions of driving face 70 not overlaid by pH-control layer 58 remain capable of effecting direct electrical contact with medicament matrix 46. As seen in FIG. 9, these portions of driving face 70 are located about the periphery of pH-control layer 58. In alternative embodiments of an active electrode embodying teachings of the present invention, portions of driving face 70 not covered by pH-control layer 58 that are, therefore, capable of effecting direct electrical contact with medicament matrix 46 can in addition or in the alternative be located interior of periphery 75 of pH-control layer 58.

Shaft 64 of stud 62 of electrical contact 38 can be seen in FIG. 9 extending through pH-control layer 58 and backing layer 56 of active electrode 54 and being captured in the interior of snap fitting 60. As a result snap fitting 60 is in direct electrical contact with securement surface 68 of backing layer 56, and flange 66 of stud 62 engages and occludes a portion of driving face 74 of pH-control layer 58. Nonetheless, the portions of driving face 74 of pH-control layer 58 located radially outwardly of the periphery of flange 66 remain capable of direct electrical contact with medicament matrix 46. The face of flange 66 from which shaft 64 projects engages driving face 74 of pH-control layer 58. Whether this engagement effects any electrical coupling with pH-control layer 58 is dependent upon whether stud 62, or at least flange 66 thereof, is made of an electrically conductive material.

The role of backing layer 56 in active electrode 54 is that of communicating to medicament matrix 46 the electrical potential that is applied to snap fitting 60 of electrical contact 38. As backing layer 56 is constructed from an electrically conductive material, that electrical potential is communicated to medicament matrix 46 directly through the peripheral edges of backing layer 56 and through driving face 70 of backing layer 56. As pH-control layer 58 is also made of an electrically conductive material, the portion of driving face 70 of backing layer 56 that is covered by pH-control layer 58 participates in this function indirectly through pH-control layer 58. To the extent that stud 62, or at least flange 66 of stud 62, is made of an electrically conductive material, the electrical potential on snap fitting 60 is communicated in part to medicament matrix 46 through flange 66.

The electrical potential imposed on backing layer 56 causes skin current $I_S$ to flow from skin 102 into medicament matrix 46 as shown in FIG. 9. From medicament matrix 46 skin current $I_S$ reaches snap fitting 60 of electrical contact 38 through backing layer 56. A portion of skin current $I_S$ enters backing layer 56 as a first constituent current $I_{56}$ that is shown in FIG. 9 to flow directly into backing layer 56 from medicament matrix 46 through the portion of driving face 70 of backing layer 56 that directly contacts medicament matrix 46. The balance of skin current $I_S$ enters backing layer 56 indirectly as a second constituent current $I_{58}$ that is shown in FIG. 9 to flow from medicament matrix 46 into backing layer 56 by way of pH-control layer 58. Second constituent current $I_{58}$ enters pH-control layer 58 through driving face 74 thereof and then passes into backing layer 56 through the portion of driving face 70 that is covered by pH-control layer 58.

The role of pH-control layer 58 in active electrode 54 is that of moderating changes in the hydrogen-ion concentration, or the pH, developed in medicament matrix 46 during the flow of skin current $I_S$. The entry of second constituent current $I_{58}$ into pH-control layer 58 from medicament matrix 46 causes some of the material of which pH-control layer 58 is comprised to migrate out of pH-control layer 58 and into medicament matrix 46 as an ionic flow $F_1$ that also appears in FIG. 9. Depending on the material composition chosen for pH-control layer 58 as described earlier, ionic flow $F_1$ serves in various ways to moderating changes in the hydrogen-ion concentration in medicament matrix 46. For example, the materials in ionic flow $F_1$ could preclude the electrolysis of the water ($H_2O$) in medicament matrix 46 by competing to be electrolyzed instead of that water ($H_2O$) during iontophoretic current flow. Alternatively, the material in ionic flow $F_1$ could neutralize the electrolysis products of water ($H_2O$) caused by iontophoretic current flow.

In this process, the material of which pH-control layer 58 is comprised gradually becomes depleted. Should pH-control layer 58 thereby become completely consumed as ionic flow $F_1$, pH-control layer 58 will no longer be reliably conductive, and may even completely block the passage of second constituent current $I_{58}$ therethrough into backing layer 56. Skin current $I_S$ correspondingly will become irregular or cease entirely. In other terms, the electrical resistance of active electrode 54 will increase, possibly to an extent that iontophoretic current flow will terminate.

Against this possibility, pH-control layer 58 and backing layer 56 are so sized and positioned relative to each other that pH-control layer 58 covers less than all of driving face 70 of backing layer 56. Then, regardless of the conditions of electrical conductivity in pH-control layer 58, the portion of driving face 70 not obscured by pH-control layer 58 offers a conductive pathway for at least first constituent current $I_{56}$, and the continuity of at least some iontophoretic current flow is insured. The electrically conductive pathway taken by first constituent current $I_{56}$ is a relative low resistance pathway as compared to the conductive pathway taken through pH-control layer 58 by second constituent current $I_{58}$, even when the material of pH-control layer 58 has not been depleted by iontophoretic current flow to any significant degree.

Therefore, the design of active electrode 54 in such a manner that a portion of driving face 70 of backing layer 56 is not covered by pH-control layer 58 reduces the overall electrical resistance to iontophoretic current flow presented by active electrode 54. Indeed, the overall resistance of active electrode 54 can be adjusted appropriately in anticipation of specific therapy conditions by varying a pair of active electrode design criteria. The first criterion is the ratio $R_{A-58}$ of the area $A_{58}$ of pH-control layer 58 to the total area $A_{E-56}$ of backing layer 56. The second criterion is the ratio $R_{E-56}$ of the area $A_{E-56}$ of the exposed portion of backing layer 56 that is not covered by pH-control layer 58 to the area $A_{58}$ of pH-control layer 58. Examples of $R_A$ and of $R_E$ will be disclosed subsequently for a number of embodiments of active electrodes configured according to teachings of the present invention.

Before doing so, however, it should be recalled that the rate of electrolysis of water ($H_2O$) is accelerated in a region 104 of medicament matrix 46 that is directly opposite from flange 66 of electrical contact 38, and that in region 104 there is an increased likelihood of pH-instability due to the eclipsing of driving face 74 of pH-control layer 58 by flange 66. If flange 66 is electrically conductive, this problem can be ameliorated by coating the surface of flange 66 that engages medicament matrix 46 with a material of the types from which pH-control layer 58 is comprised. Alternatively, stud 62 of electrical contact 38, or at least flange 66 of stud 62, can be fabricated from a material that is electrically insulative.

FIGS. 10A-10F are plan views of individual embodiments of active electrodes incorporating teachings of the present invention taken from the side of each respective active electrode that engages the medicament reservoir, such as medicament matrix 46, in an active medicament patch. In each case, the active electrode depicted is shown resting against, and possibly secured to, the underlying therapeutic face 40 of a substrate of a medicament patch.

Figures 10A, 10B:
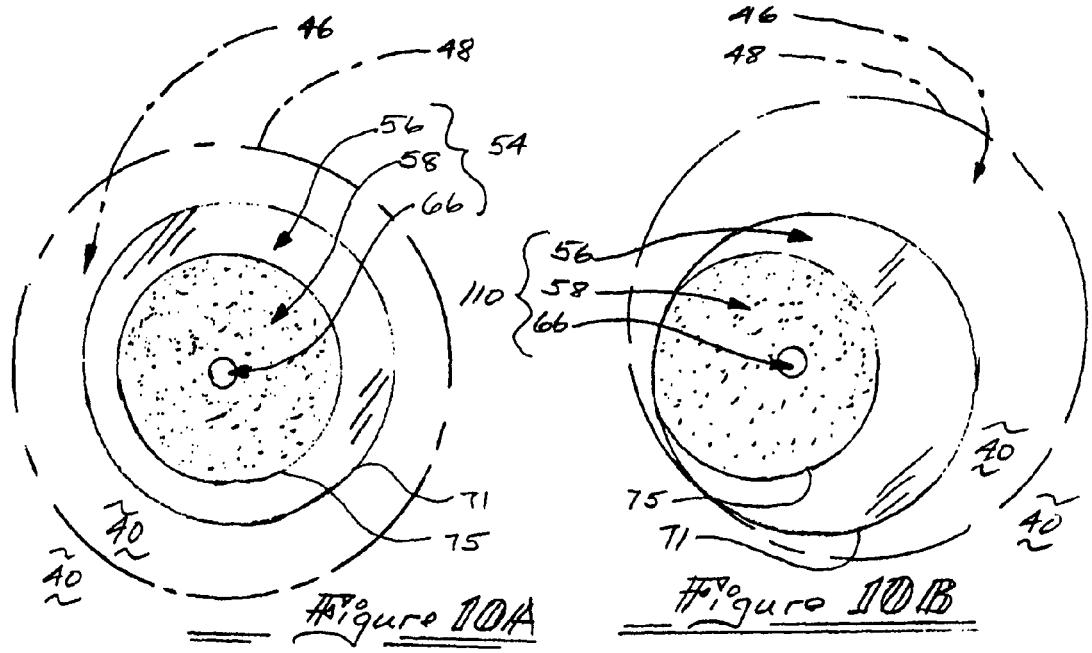
FIGS. 10A-10F are plan views of individual embodiments of active electrodes incorporating teachings of the present invention taken from the side of each respective active electrode that engages the medicament reservoir of an active medicament patch, FIG. 10A being such a view of the active electrode of FIG. 9.

FIG. 10A is such a plan view of active electrode 54 of FIG. 9. Superimposed by way of reference in phantom on therapeutic face 40 is periphery 48 of medicament matrix 46, which in the assembled condition of the medicament patch depicted would entirely obscure active electrode 54. This is borne out in FIG. 10A, as flange 66 of stud 62 of electrical contact 38, pH-control layer 58, and backing layer 56 of active electrode 54 are shown superimposed on one another in that order, with all of each of these components of active electrode 54 located interior of periphery 48 of medicament matrix 46.

Periphery 71 of backing layer 56, periphery 75 of pH-control layer 58, and periphery 48 of medicament matrix 46 are each generally circular in configuration. Nonetheless, periphery 71, periphery 75, and periphery 48 are not, and need not be, disposed in any concentric relationship to each other, or to flange 66 of stud 62 of electrical contact 38. The total area $A_{56}$ of backing layer 56 is greater than the area $A_{58}$ of pH-control layer 58. Periphery 75 of pH-control layer 58 is disposed entirely within periphery 71 of backing layer 56, and backing layer 56 has an exposed annular area $A_{E-56}$ between periphery 75 of pH-control layer 58 and periphery 71 that is not covered by pH-control layer 58. The active electrode design criteria for active electrode 54 as defined earlier are approximately as follows:

$$R_{A-58}=0.70; \text{ and}$$

$$R_{E-56}=2.35.$$

FIG. 10B is a plan view of a second embodiment of an active electrode 110 incorporating teachings of the present invention. Superimposed by way of reference in phantom on therapeutic face 40 is periphery 48 of medicament matrix 46, which in the assembled condition of the medicament patch depicted would entirely obscure active electrode 110.

Active electrode 110 is made up of the same elements, namely flange 66 of stud 62 of electrical contact 38, pH-control layer 58, and backing layer 56, as were employed in active electrode 54 in FIG. 10A. In contrast thereto, however, these elements are more pronouncedly eccentrically positioned relative to each other and to periphery 48 of medicament matrix 46 than was the case relative to active electrode 54 in FIG. 10A.

In FIG. 10B, periphery 75 of pH-control layer 58 tangentially engages periphery 71 of backing layer 56 at a single point, and periphery 71 of backing layer 56 tangentially engages periphery 48 of medicament matrix 46 at a single point. As thusly arranged, medicament matrix 46 would nonetheless entirely obscure active electrode 110. The total area $A_{56}$ of backing layer 56 remains greater than the area $A_{58}$ of pH-control layer 58, and backing layer 56 has an exposed crescentic area $A_{E-56}$ not covered by pH-control layer 58 between periphery 75 of pH-control layer 58 and periphery 71 of backing layer 56. The active electrode design criteria for active electrode 110 as defined earlier remain approximately as follows:

$$R_{A-58}=0.70; \text{ and}$$

$$R_{E-56}=2.35.$$

Figures 10C, 10D:
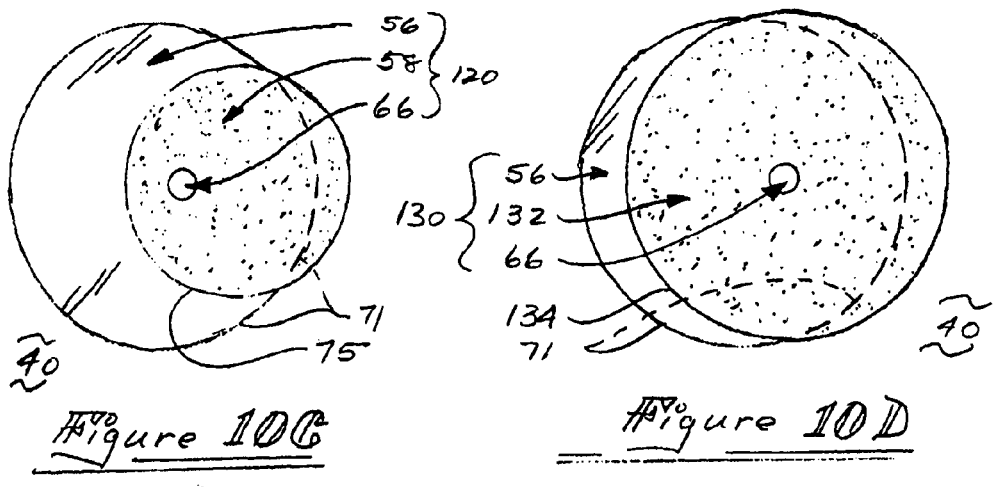

FIG. 10C is a plan view of a third embodiment of an active electrode 120 incorporating teachings of the present invention. In contrast to FIGS. 10A and 10B, no phantom rendition of periphery 48 of medicament matrix 46 is included in FIG. 10C or in any subsequent figures.

Active electrode 120 is made up of the same elements, namely flange 66 of stud 62 of electrical contact 38, pH-control layer 58, and backing layer 56, as were employed in active electrode 54 in FIG. 10A. In contrast thereto, however, while backing layer 56 continues to be covered in part only by pH-control layer 58, periphery 75 of pH-control layer 58 extends to the exterior of periphery 71 of backing layer 56. These are nonetheless acceptable relationships among components in an active electrode.

The total area $A_{56}$ of backing layer 56 remains greater than the area $A_{58}$ of pH-control layer 58, and backing layer 56 has an exposed crescentic area $A_{E-56}$ between periphery 75 of pH-control layer 58 and periphery 71 that is not covered by pH-control layer 58. The active electrode design criteria for active electrode 120 as defined earlier are approximately as follows:

$$R_{A-58}=0.70; \text{ and}$$

$$R_{E-56}=1.40.$$

FIG. 10D is a plan view of a fourth embodiment of an active electrode 130 incorporating teachings of the present invention.

Active electrode 130 is made up of the same flange 66 of stud 62 of electrical contact 38 and the same backing layer 56 as were employed in active electrode 54 in FIG. 10A. In FIG. 10D by contrast, a pH-control layer 132 is included in active electrode 130 that is of approximately the same size and shape as backing layer 56. Thus, pH-control layer 132 has a periphery 134 that is approximately congruent with periphery 71 of backing layer 56. These nonetheless are acceptable relationships among components in an active electrode.

The total area $A_{56}$ of backing layer 56 is approximately equal to the area $A_{132}$ of pH-control layer 132. Backing layer 56 has an exposed crescentic area $A_{E-56}$ that is not covered by pH-control layer 132 between periphery 134 of pH-control layer 132 and periphery 71 of backing layer 56. The active electrode design criteria for active electrode 130 as defined earlier are approximately as follows:

$$R_{A-32}=1.00; \text{ and}$$

$$R_{E-56}=8.00.$$

Figures 10E, 10F:
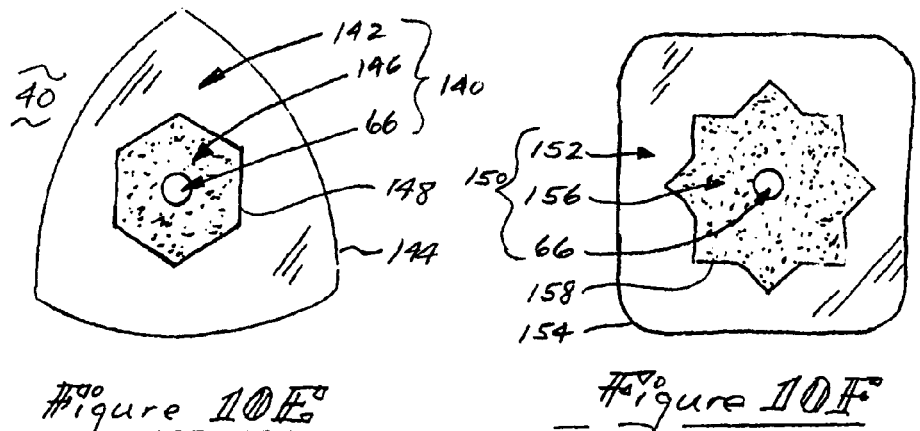

FIG. 10E is a plan view of a fifth embodiment of an active electrode 140 incorporating teachings of the present invention.

Active electrode 140 is made up of the same flange 66 of stud 62 of electrical contact 38 used in earlier embodiments, in addition to a backing layer 142 having a curved, generally triangular periphery 144 with three vertices and a pH-control layer 146 having a hexagonal periphery 148. Flange 66 of stud 62 of electrical contact 38, pH-control layer 146, and backing layer 142 of active electrode 140 are shown superimposed on one another in that order is a generally concentric manner.

The total area $A_{142}$ of backing layer 142 is greater than the area $A_{146}$ of pH-control layer 146. Periphery 148 of pH-control layer 146 is disposed entirely within periphery 144 of backing layer 142. Backing layer 142 has an exposed area $A_{E-142}$ that is not covered by pH-control layer 146 and that assumes an irregular, generally annular shape bounded on the interior by periphery 148 of pH-control layer 146 and on the exterior by periphery 144 of backing layer 142. The active electrode design criteria for active electrode 140 as defined earlier are approximately as follows:

$$R_{A-146}=0.15; \text{ and}$$

$$R_{E-142}=0.20.$$

FIG. 10F is a plan view of a sixth embodiment of an active electrode 150 incorporating teachings of the present invention.

Active electrode 150 is made up of the same flange 66 of stud 62 of electrical contact 38 used in earlier embodiments, in addition to a backing layer 152 having a generally squarish periphery 154 with rounded corners and a pH-control layer 156 having a star-shaped, polygonal periphery 158 with eight points. Flange 66 of stud 62 of electrical contact 38, pH-control layer 156, and backing layer 152 of active electrode 150 are shown superimposed on one another in that order in a somewhat concentric manner.

The total area $A_{152}$ of backing layer 152 is greater than the area $A_{156}$ of pH-control layer 156. Periphery 158 of pH-control layer 156 is disposed entirely within periphery 154 of backing layer 152. Backing layer 152 has an exposed area $A_{E-152}$ that is not covered by pH-control layer 156 and that assumes an irregular, but somewhat annular shape bounded on the interior by periphery 158 of pH-control layer 156 and on the exterior by periphery 154 of backing layer 152. The active electrode design criteria for active electrode 150 as defined earlier are approximately as follows:

$$R_{A-156} = 0.35; \text{ and}$$

$$R_{E-152} = 0.50.$$

FIG. 11 shows patient 10 again requiring the localized administration of a medicament, but in this instance to knee 160 thereof. For that purpose, patient 10 is wearing on knee 160 elements of a second embodiment of an active iontophoretic delivery system 166 that incorporates teachings of the present invention. While so doing, patient 10 is nonetheless able to engage in extended and repeated, vigorous physical activities, because delivery system 166 is entirely self-contained, not even being supplied with electric power from an external source. Delivery system 166 includes only an active transdermal medicament patch 168 that carries all of the elements of delivery system 166.

Medicament patch 168 is removable adhered to the skin of knee 160 of patient 10 at the location at which the need for the administration of medicament is most acute. Medicament patch 168 carries a medicament reservoir filled with a medicament solution, a power source, an active electrode by which the electrical potential at an appropriate pole of that power source is communicated to and through the medicament reservoir to the skin of patient 10, and a return electrode by which the electrical potential at the other pole of the power source is communicated to the skin of patient 10 at a contact location remote from the medicament reservoir.

FIGS. 12-15 taken together afford an overview of the structure of the elements of medicament patch 168.

Figure 11:
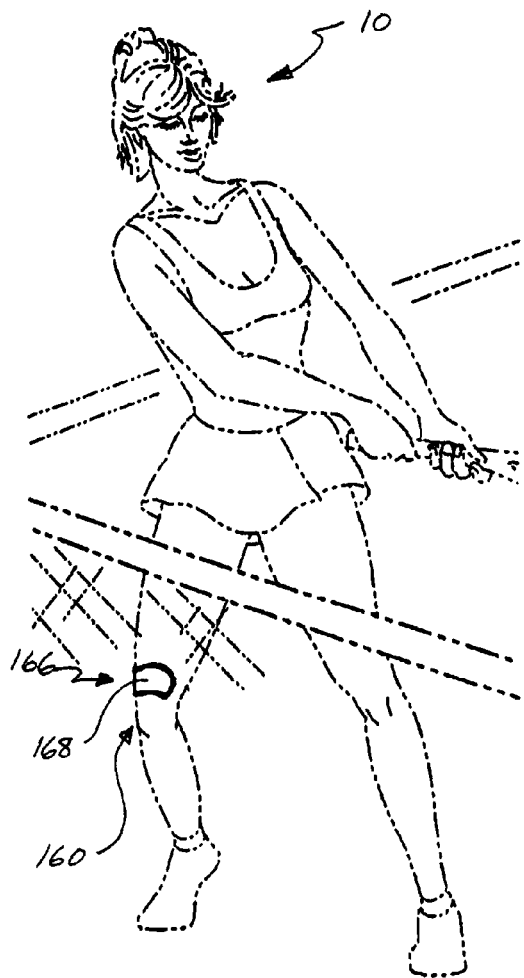
FIG. 11 is a perspective view of a fully-integrated, second embodiment of an active iontophoretic transdermal patch incorporating teachings of the present invention and being worn by a patient requiring the localized administration of a medicament.
Figure 12:
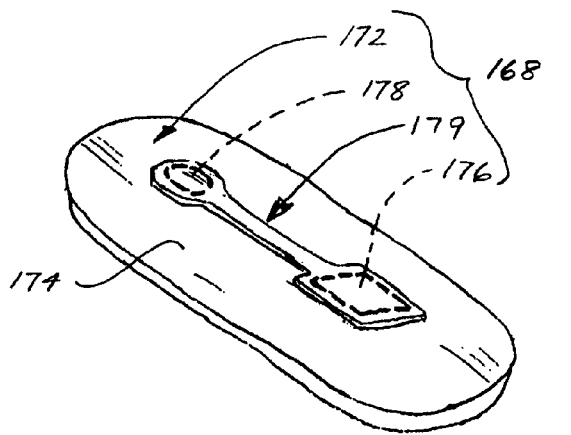
FIG. 12 is a perspective view of the active transdermal patch of the FIG. 11 showing the upper face of the substrate of the patch that is visible when the patch is worn on the person of a patient.

FIG. 12 is a perspective view of medicament patch 168 showing the surface of medicament patch 168 that is exposed when medicament patch 168 is worn by patient 10 in the manner illustrated in FIG. 11. Thus, medicament patch 168 includes a flexible, planar biocompatible, non-electrically conductive, oval substrate 172 that has an upper face 174 that is visible when worn by patient 10. Upper face 174 of substrate 172 carries electronic circuitry 176 and a corresponding power source 178 that are electrically interconnected to each other along upper face 174 of substrate 172. By way of example, power source 178 could be one or a plurality of series-connected miniature batteries, each of about 3 volts potential. Power source 178 thus supplies non-alternating current to electronic circuitry 176. Electronic circuitry 176 and power source 178 are shown as being encased on upper face 174 of substrate 172 by an opaque protective cover 179, but either or both of power source 178 and electronic circuitry 176 could with equal functional adequacy be partially or wholly imbedded in substrate 172, or even carried on the side thereof opposite form upper face 174.

Figure 13:
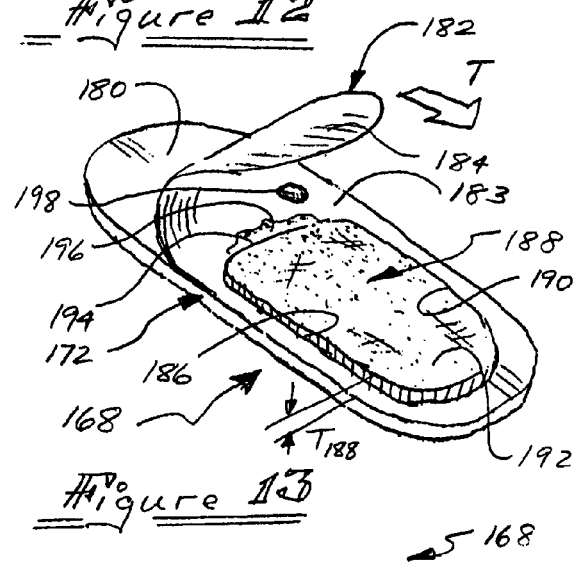
FIG. 13 is a perspective view of the active transdermal patch of FIG. 12 depicting the therapeutic face of the substrate of the patch on the side thereof opposite that in FIG. 12 and showing a release liner in the process of being peeled from the adhesive on the therapeutic face.

FIG. 13 is a perspective view of medicament patch 168 taken from the side thereof opposite from that of upper face 174 shown in FIG. 12. Revealed thusly is a therapeutic face 180 of substrate 172 that is intended to be disposed in contact with the skin of a patient. Therapeutic face 180 is coated with a biocompatible adhesive to a sufficient extent as to enable therapeutic face 180 to be removably secured to the person of patient 10. Prior to the actual use of medicament patch 168, the adhesive on therapeutic face 180 is shielded by a removable release liner 182, which as suggested by arrow T in FIG. 13 is in the process of being peeled from therapeutic face 180. Release liner 182 has on the opposite sided thereof, respectively, first an exposed face 183 and second a contact face 184 that actually engages the adhesive on therapeutic face 180 of substrate 172.

Formed generally centrally through release liner 182 is a medicament matrix aperture 186. As shown in FIG. 13, medicament matrix aperture 186 is substantially filled by a generally planar medicament matrix 188 that exhibits a periphery 190 having an elongated D-shape with rounded corners. Medicament matrix 188 can take the form of a gel suspension of medicament or of an absorbent pad of gauze or cotton that is saturated at some time prior to use with a fluid solution containing medicament. When permeated by a medicament, medicament matrix 188 functions as the medicament reservoir of medicament patch 168.

The side of medicament matrix 188 visible in FIG. 13 forms a correspondingly elongated D-shaped skin contact surface 192 interior of periphery 190. Medicament matrix 188 projects through medicament matrix aperture 186 in such a manner that skin contact surface 192, while oriented generally parallel to the plane of release liner 182 and the plane of therapeutic face 180 of substrate 172, is separated from each by a distance that is substantially equal to the thickness $T_{188}$ of medicament matrix 188. Medicament matrix 188 is intended by way of skin contact surface 192 thereof to electrically conductively engage the skin of a patient, when therapeutic face 180 of substrate 172 is disposed against and removably adhered to the person of the patient.

Medicament matrix aperture 186 in release liner 182 and medicament matrix 188 on therapeutic face 180 of substrate 172 are closely similar in size and shape. As a result, in FIG. 13 the edges of medicament matrix aperture 186 are in close proximity to periphery 190 of medicament matrix 188, when contact face 184 of release liner 182 is disposed covering the adhesive on the portion of therapeutic face 180 located outwardly from periphery 190 of medicament matrix 188.

Medicament matrix aperture 186 in release liner 182 configured in this manner affords unimpeded access by medical personnel to the entirety of skin contact surface 192 of medicament matrix 188 prior to the removal of release liner 182 from therapeutic face 180, and in particularly during wetting of medicament matrix 188 with a medicament solution in anticipation of the actual use of medicament patch 168. While the saturated portion of medicament matrix 188 grows during wetting, a medical practitioner is able to observe the enlargement of that saturated portion as drops of medicament solution are added to medicament matrix 188, eventually to verify that the entirety of medicament matrix 188 is adequately wetted.

Additionally, the near congruency of periphery 190 of skin contact surface 192 of medicament matrix 188 with medicament matrix aperture 186 in release liner 182 advantageously allows release liner 182 to protect the adhesive on the exposed portion of therapeutic face 180 from any medicament solution that might overflow from medicament matrix 188 during the wetting thereof prior to the actual use of medicament patch 168.

It is not uncommon that a medicament matrix, such as medicament matrix 188, becomes locally oversaturated with medicament solution in some areas during this process. Then, being unable to be contained in medicament matrix 188, some of the deposited medicament solution in medicament matrix 188 will overflow medicament matrix 188 at periphery 190 thereof. This overflow of medicament solution does not contact the adhesive on substrate 172, but rather is deposited on exposed face 183 of release liner 182. Such a situation is illustrated in FIG. 13, where the lateral expansion of the saturated portion of medicament matrix 188 has reached a section 194 of periphery 190 of medicament matrix 188 in advance of the balance of periphery 190. As a consequence, an overflow 196 of medicament solution is discharged from medicament matrix 188 through section 194 of periphery 190 onto exposed face 183 of release liner 182.

Frequently during the process of wetting a medicament matrix, such as medicament matrix 188, droplets of medicament solution become inadvertently deposited on exposed face 183 of medicament patch 168 remote from medicament matrix 188. Such droplets are also precluded from contacting the adhesive on therapeutic face 180 of substrate 172 by release liner 182. Such a droplet 198 of medicament solution is shown in FIG. 12.

Medicament solution that is not deposited on contact face 184 of medicament matrix aperture 186, or if deposited on medicament matrix 188, that is not retained therewithin, is automatically removed from medicament patch 168 prior the disposition of therapeutic face 180 of substrate 172 against the skin of a patient through the peeling of release liner 182 from medicament patch 168 in the manner indicated in FIG. 13 by arrow T. This safe disposal of excess medicament solution was illustrated in FIGS. 7A-7C and discussed there relative to first overflow 90, second overflow 92, and droplets 94.

Thus, release liner 182 configured and assembled in the manner illustrated, with medicament matrix aperture 186 closely surrounding periphery 190 of medicament matrix 188, preserves the capacity of the exposed adhesive on substrate 172 to reliably adhere to the skin of a patient. In so doing, release liner 182 also maintains the capacity of that adhesive to electrically insulate medicament matrix 186 in the plane of the skin of the patient, once medicament patch 168 is adhered thereto. Were that adhesive to become wetted with medicament solution before being used to adhere medicament patch 168 to the skin, then the electrically conductive pathways arising in the medicament solution between medicament patch 168 and the skin would render the active electrode carried on medicament patch 168 susceptible to being shorted along the surface of the skin to the return electrode that is also carried thereby.

Figure 14:
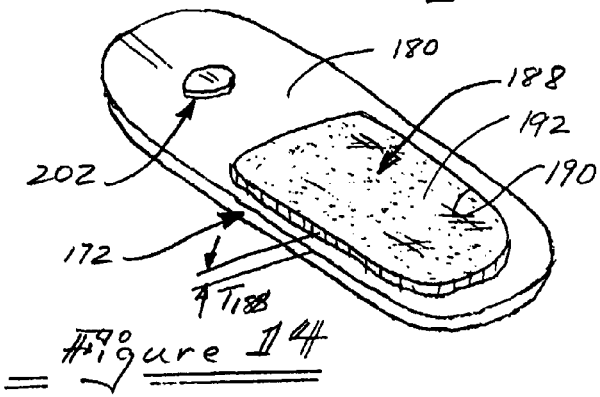
FIG. 14 is a perspective view of the therapeutic face of the active transdermal patch of FIG. 13 with the release liner illustrated in FIG. 13 fully removed.

FIG. 14 shows therapeutic face 180 of substrate 172 after the complete removal of release liner 182 therefrom. Medicament matrix 188 is positioned on therapeutic face 180 of substrate 172 with periphery 190 of medicament matrix 186 interior of the periphery 200 of therapeutic face 180. Medicament matrix 186 is non-releasably retained there by the same adhesive that necessitates the use of release liner 182, or by any other appropriate arrangement. Medicament matrix 186 thus obscures a portion of therapeutic face 180 of substrate 172 that is concealed from view in FIG. 14. The balance of therapeutic face 180, the portion located outwardly from periphery 190 of medicament matrix 186, is the portion of therapeutic face 180 that is exposed to view in FIG. 14 but that was covered substantially entirely by release liner 182 in FIG. 13.

A return electrode 202 can be seen in FIG. 14 to also be positioned on therapeutic face 180 of substrate 172, but electrical return electrode 202 is separated from medicament matrix 188, and thus electrically isolated therefrom by the adhesive covering therapeutic face 180 of substrate 172 therebetween. Return electrode 202 is also capable of electrically conductively engaging the skin of patient 10 when therapeutic face 180 of substrate 172 is disposed against the skin. Accordingly, when as shown in FIG. 11, medicament patch 168 is adhered to the skin of patient 10, return electrode 202 engages the skin of patient 10 at a location that is remote from medicament matrix 188.

FIG. 15 is a partially-exploded perspective view of medicament patch 168 of FIG. 14. Medicament matrix 188 is there depicted above and separated from therapeutic face 180 of substrate 172. Revealed thereby as resting against, and possibly secured to, therapeutic face 180 of substrate 172 is a seventh embodiment of and active electrode 210 embodying teachings of the present invention. Active electrode 210 includes a planar backing layer 212 having a snowshoe-shaped periphery 214 and a generally elliptical, planar pH-control layer 216 with a periphery 218 disposed there against. Superimposed by way of reference in phantom on therapeutic face 180 is periphery 190 of medicament matrix 186, which in the assembled condition of medicament patch 168 shown in FIG. 14 entirely obscures active electrode 210. This is borne out in FIG. 15, as pH-control layer 216 and backing layer 212 of active electrode 210 are shown superimposed on one another in that order, with all of each component of active electrode 210 located interior of periphery 190 of medicament matrix 186.

Two points of periphery 218 of pH-control layer 216 tangentially engage distinct locations on periphery 214 of backing layer 212. Therefore, pH-control layer 216 covers less than all of backing layer 212, and pH-control layer 216 separates the exposed portion of backing layer 212 into a pair of non-congruent regions 219, 220, to either lateral side of pH-control layer 216.

The total area $A_{212}$ of backing layer 212 is greater than the area $A_{216}$ of pH-control layer 216. Backing layer 212 has an exposed area $A_{E-212}$ not covered by pH-control layer 216 that includes regions 219, 220, of backing layer 212 between respective paired sections of periphery 218 of pH-control layer 216 and periphery 214 of backing layer 212. The active electrode design criteria for active electrode 210 as defined earlier are approximately as follows:

$$R_{A-216}=0.35; \text{ and}$$

$$R_{E-214}=2.00.$$

It is noteworthy that active electrode 210 includes no electrical contact of the two-part type appearing in embodiments of active electrodes disclosed earlier. The electrical potential of power source 178 of medicament patch 168 is communicated to backing layer 212 and therethrough to pH-control layer 216 using other arrangements that will be illustrated in subsequent figures. Therefore, no flange of any stud employed in such a two-part structure covers any portion of pH-control layer 216 in FIG. 15.

FIG. 16 is an elevation cross-sectional view of the elements of medicament patch 168 of FIG. 15 in an assembled condition and taken along section line 16-16 therein.

As a result, FIG. 16 depicts in edge view both upper face 174 and therapeutic face 180 substrate 172, as well as the interaction therethrough of each of the elements of delivery system 166 carried by medicament patch 168. Reservoir 188 is shown as being carried on therapeutic face 180 of substrate 172, while electronic circuitry 176 and power source 178 encased in cover 179 are shown carried on upper face 174.

Similarly, return electrode 202 is shown as being carried on therapeutic face 180 and as including a conductive layer 220 that is immediately adjacent to therapeutic face 180 and an ionic exchange layer 222. Ionic exchange layer 222 of active electrode 210 covers the side of conductive layer 220 remote from therapeutic face 180, as well as the portion of therapeutic face 180 immediately surrounding conductive layer 220. Typically, conductive layer 220 is made from a film of an electrically conductive material, such as carbon (C), copper (Cu), aluminum (Al), or rubberized carbon. Ionic exchange layer 222 can take the form of a gel suspension or of an absorbent pad of gauze or cotton that is saturated before use with an electrically conductive fluid solution.

Based on the polarity of the medicament to be administered using medicament patch 168, one of electronic circuitry 176 and power source 178 is electrically interconnected by way of a first via 224 through substrate 172 to backing layer 212 of active electrode 210. The other of electronic circuitry 176 and power source 178 is electrically interconnected by way of a second via 226 through substrate 172 to conductive layer 220 of return electrode 202. If either or both of power source 178 and electronic circuitry 176 is partially or wholly imbedded in substrate 172 or carried on therapeutic face 180, the need for either or both of first via 224 and second via 226 may be obviated.

FIG. 17 has been included by way of example to illustrate the movement of molecules of medicament, when medicament patch 168 is used to administer a negative medicament M⁻. The use of medicament patch 168 to administer a positive medicament M⁺ will not be illustrated in view of the understandings already provided above in relation to FIG. 8A about the administration of a positive medicament M⁺ using medicament patch 18 and auxiliary patch 20 of delivery system 17.

In FIG. 17, therapeutic face 180 of substrate 172 of medicament patch 168 is shown as being disposed against surface 100 of skin 102. Thus, medicament matrix 188 and conductive layer 220 of ionic exchange layer 222 each electrically conductively engage surface 100 of skin 102, but at locations that are separated from each other. Aside from the conductivity of skin 102, these locations are electrically isolated from each other.

While the structural details of power source 178 are not presented in FIG. 17, it is necessary in using medicament patch 168 to administer a negative medicament M⁻ that the negative pole P⁻ of power source 178 be coupled through electronic circuitry 176, first via 224, and active electrode 210 to medicament matrix 188. The positive pole P⁺ of power source 178 is in turn coupled by way of second via 226 to return electrode 202. The electromotive differential thusly applied to skin 102 between medicament matrix 188 and return electrode 202 induces molecules of negative medicament M⁻ to move as negative ions out of medicament matrix 188 toward skin 102, across the unbroken surface 100 of skin 102, and through skin 102 in the direction of return electrode 202. This movement is indicated in FIG. 17 by a dashed arrow labeled M⁻. A skin current $I_S$ is schematically indicated by a solid arrow to flow through skin 102 from return electrode 202 that is associated electrically with the positive pole P⁺ of power source 176 to medicament matrix 188 that is associated electrically with the negative pole P⁻ of power source 176.

FIGS. 18A-18D are plan views of individual embodiments of active electrodes incorporating teachings of the present invention taken from the side of each respective active electrode that engages a medicament reservoir, such as medicament matrix 188, in an active medicament patch. In each case, the active electrode is shown resting against, and possibly secured to, the underlying therapeutic face 180 of a substrate, such as substrate 172, of a medicament patch, such as medicament patch 168 of FIGS. 12-17. In the assembled condition of the medicament patch in which the active electrode is employed, a medicament matrix, such as medicament matrix 188 from FIGS. 11-17, would be superimposed over the active electrode and secured about the periphery of the active electrode to therapeutic face 180 entirely obscuring the active electrode.

Figure 18A:
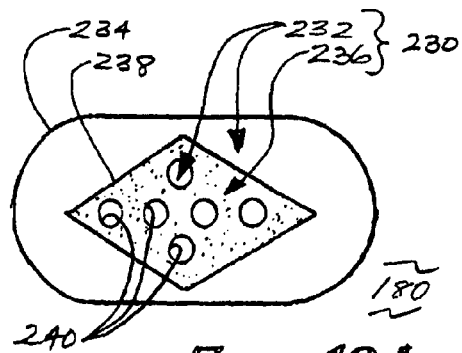
FIGS. 18A-18D are plan views of individual embodiments of active electrodes incorporating teachings of the present invention taken from the side of each respective active electrode that engages the medicament reservoir of an active medicament patch.

FIG. 18A is such a plan view of an eighth embodiment of an active electrode 230 incorporating teachings of the present invention.

Active electrode 230 includes a backing layer 232 having a generally oval periphery 234. Superimposed on backing layer 232 is a pH-control layer 236 that has a generally rhomboidal periphery 238. Formed through pH-control layer 236 is a plurality of circular apertures 240 at which the surface of backing layer 232 against which pH-control layer 236 is disposed is nonetheless free of pH-control layer 236.

The total area $A_{232}$ of backing layer 232 is greater than the area $A_{236}$ of pH-control layer 236. Periphery 238 of pH-control layer 236 is disposed entirely interior of periphery 234 of backing layer 232. Backing layer 232 has an exposed area $A_{E-232}$ not covered by pH-control layer 236 that includes the area between periphery 238 of pH-control layer 236 and periphery 234 of backing layer 232 in addition to all of the areas within apertures 240. The active electrode design criteria for active electrode 230 as defined earlier are approximately as follows:

$R_{A-236} = 0.25$; and $R_{E-232} = 0.20$.

Figure 18B:
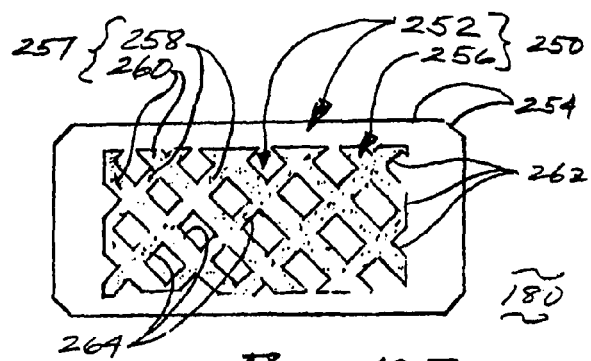

FIG. 18B is a plan view of a ninth embodiment of an active electrode 250 incorporating teachings of the present invention.

Active electrode 250 includes a backing layer 252 having a generally rectangular periphery 254 with beveled corners. Superimposed on backing layer 252 is a pH-control layer 256 of overall, generally rectangular extent. In detail, however, pH-control layer 256 is a lattice 257 of orthogonally crossing narrow slats 258 and wide slats 260. Consequently, the periphery 262 of pH-control layer 256 is an irregular, complex polygon. As a consequence of the lattice structure of pH-control layer 256, a plurality of apertures 264 are formed through pH-control layer 256 at which the surface of backing layer 252 against which pH-control layer 256 is disposed is nonetheless free of pH-control layer 256. Each aperture 264 is bounded by an adjacent pair of narrow slats 258 and an adjacent pair of wide slats 260.

The total area $A_{252}$ of backing layer 252 is greater than the area $A_{256}$ of pH-control layer 256. Periphery 262 of pH-control layer 256 is disposed entirely interior of periphery 254 of backing layer 252. Backing layer 252 has an exposed area $A_{E-252}$ not covered by pH-control layer 256 that includes the area between periphery 262 of pH-control layer 256 and periphery 254 of backing layer 252 in addition to all of the areas within apertures 264. The active electrode design criteria for active electrode 250 as defined earlier are approximately as follows:

$R_{A-256} = 0.50$; and $R_{E-252} = 0.35$.

Figure 18C:
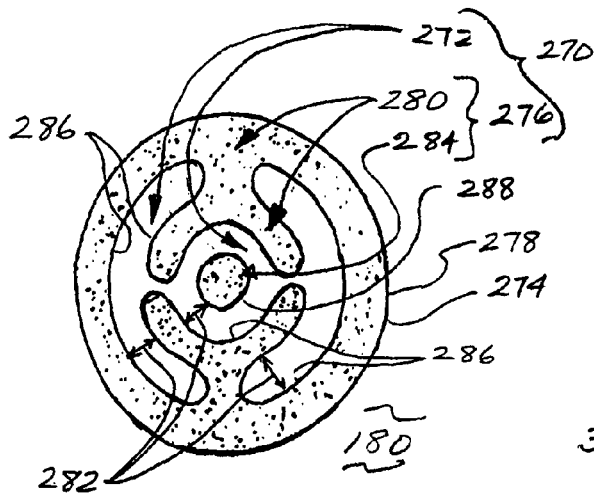

FIG. 18C is a plan view of a tenth embodiment of an active electrode 270 incorporating teachings of the present invention Active electrode 270 includes a backing layer 272 having a generally circular periphery 274. Superimposed on backing layer 272 is a pH-control layer 276 of an overall, generally circular extent with a periphery 278 that is congruent to and coincident with periphery 274 of backing layer 272. In detail, however, pH-control layer 276 is made up of a plurality of discrete, unconnected components that cover a corresponding plurality of discrete, unconnected portions of the surface of backing layer 272 appearing in FIG. 18C. The discrete, unconnected components of pH-control layer 276 include an outer component 280 having a substantial aperture 282 formed therethrough and an inner component 284 that is positioned on the portion of the surface of backing layer 272 that appears through aperture 282. Aperture 282 has an extended, complexly curved periphery 286, while inner component 284 of pH-control layer 276 has a generally circular periphery 288.

The total area $A_{272}$ of backing layer 272 is greater than the area $A_{276}$ of pH-control layer 276. The only area of backing layer 272 not covered by pH-control layer 276 is an exposed area $A_{E-272}$ between periphery 288 of inner component 284 of pH-control layer 256 and periphery 286 of aperture 282 formed through pH-control layer 276. The active electrode design criteria for active electrode 270 as defined earlier are approximately as follows:

$R_{A-276}=0.70$; and $R_{E-272}=0.45$.

Figure 18D:
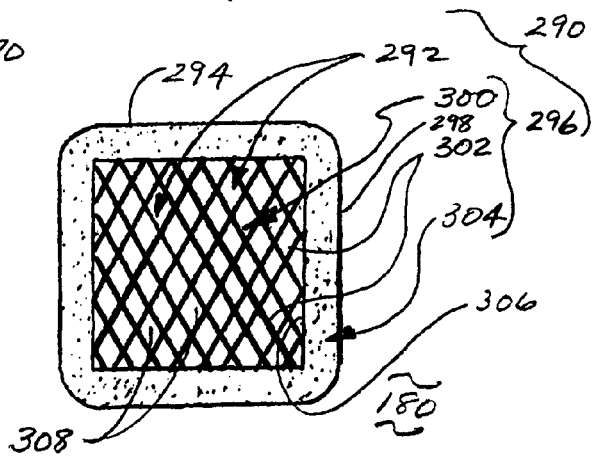

FIG. 18D is a plan view of an eleventh embodiment of an active electrode 290 incorporating teachings of the present invention.

Active electrode 290 includes a backing layer 292 having a generally squarish periphery 294 with rounded corners. Superimposed on backing layer 292 is a pH-control layer 296 of an overall, generally squarish extent with a periphery 298 that is coincident with periphery 294 of backing layer 292. In detail, however, pH-control layer 296 is a mesh 300, or field, of crossing grid lines 302, bounded by a generally square frame 304 having a square-shaped inner edge 306. As a consequence, a plurality of apertures 308 are formed through mesh 300 of pH-control layer 296 at which the surface of backing layer 292 against which pH-control layer 296 is disposed is nonetheless free of pH-control layer 296. Each aperture 308 is bounded by adjacent crossing pair of grid lines 302.

The total area $A_{292}$ of backing layer 292 is greater than the area $A_{296}$ of pH-control layer 296. Backing layer 292 has an exposed area $A_{E-292}$ not covered by pH-control layer 296 that includes all of the areas within apertures 308. All of these areas are located within inner edge 306 of frame 304 of pH-control layer 296. The active electrode design criteria for active electrode 290 as defined earlier are approximately as follows:

$R_{A-296}=0.60$; and $R_{E-292}=1.50$.

Finally, the present invention also includes the methods of manufacture necessary to provide the inventive embodiments described above, as well as methods associated with the effective therapeutic use of any of those inventive embodiments.

The invention may be embodied in other specific forms without departing from the spirit or essential characteristics thereof. The described embodiments are to be considered in all respects only as illustrative and not restrictive. The scope of the invention is, therefore, to be defined by the appended claims, rather than by the foregoing description. All variations from the literal recitations of the claims that are, nonetheless, within the range of equivalency correctly attributable to the literal recitations are, however, to be considered to be within the scope of those claims.

What is claimed is:

1. An active electrode for a medicament patch of the type including a flexible, planar biocompatible substrate with a therapeutic face for disposition against the skin of a patient and a planar medicament matrix having on respective opposite sides thereof a skin contact surface and a securement surface, the securement surface being retained against the therapeutic face of the substrate obscuring a concealed portion thereof with the balance of the therapeutic face defining an exposed portion thereof, the skin contact surface of the medicament matrix effecting electrically conductive engagement with the skin of the patient, when the exposed portion of the therapeutic face of the substrate is retained there against and the medicament matrix is permeated by a medicament, wherein said active electrode is capable of assembly in the medicament patch between the medicament matrix and the concealed portion of the therapeutic face of the substrate, and said active electrode comprises:
(a) an electrically conductive backing layer having on respective opposite sides thereof a driving face and a securement surface, said securement surface becoming positioned against the concealed portion of the therapeutic face of the substrate, when said active electrode is assembled in the medicament patch; and
(b) a pH-control layer on said driving face of said backing layer covering less than all of said driving face of said backing layer, said pH-control layer and the portion of said driving face free of said pH-control layer together electrically engaging the medicament matrix, said pH-control layer being made of an electrically conductive material capable of moderating changes in the hydrogen-ion concentration in the medicament matrix, when the therapeutic face of the substrate is disposed against the skin of the patient, and an electrical potential is imposed between said backing layer and the skin of the patient remote from the medicament matrix.

2. An active electrode as recited in claim 1, wherein said active electrode further comprises an electrical contact electrically coupled to the securement surface of said backing layer, and said electrical contact comprises:
(a) a hollow, electrically conductive snap fitting having an open end; and
(b) a cooperating, electrically insulative stud, in the assembled condition of said electrical contact said stud being inserted into said snap through said open end thereof.

3. An active electrode for a medicament patch of the type including a flexible, planar biocompatible substrate with a therapeutic face for disposition against the skin of a patient and an absorbent medicament matrix non-releasably retained against a portion of the therapeutic face of the substrate obscuring a concealed portion thereof with the balance of the therapeutic face defining an exposed portion thereof, the medicament matrix effecting electrically conductive engagement with the skin of a patient, when the exposed portion of the therapeutic face is retained there against and the medicament matrix is wetted with a medicament solution, wherein said active electrode is capable of assembly in the medicament patch between the medicament matrix and the concealed portion of the therapeutic face of the substrate, and said active electrode comprises:
(a) an electrical contact;
(b) a pH-control layer comprised of an electrically conductive material capable of moderating changes in the hydrogen-ion concentration in the medical matrix, when the patch is disposed against the skin of the patient and an electrical potential is imposed between said electrical contact and the skin of a patient at a location remote from the medicament matrix; and
(c) an electrically conductive backing layer sandwiched between said electrical contact and said pH-control layer, the surface of said backing layer contacted by said pH-control layer defining a driving face of said backing layer, and said pH-control layer covering less than all of said driving face.

4. An active electrode as recited in claim 3, wherein said pH-control layer is comprised of a material capable of precluding electrolysis in the medical matrix, when an electrical potential is imposed between said backing layer and the skin of a patient with the medicament patch disposed there against.

5. An active electrode as recited in claim 3, wherein said pH-control layer is comprised of a material capable of neutralizing electrolysis products in the medical matrix, when an electrical potential is imposed between said backing layer and the skin of a patient with the medicament patch disposed there against.

6. An active electrode as recited in claim 3, wherein said electrical contact is electrically coupled to a securement surface of said backing layer located on the side thereof opposite from said driving face.

7. An active electrode as recited in claim 6, wherein said electrical contact comprises an assembly of:
  (a) a hollow, electrically conductive snap fitting having an open end; and
  (b) a cooperating stud, in the assembled condition of said electrical contact said stud being inserted into said snap through said open end thereof.

8. An active electrode as recited in claim 7, wherein said stud is electrically insulative.

9. An active electrode as recited in claim 8, wherein said stud comprises:
  (a) a shaft configured for press fit insertion through said open end of said snap fitting; and
  (b) a generally planar flange secured to one end of said shaft.

10. An active electrode as recited in claim 9, wherein, in said assembled condition of said electrical contact, said flange of said stud is positioned on the side of said pH-control layer opposite from said driving face of said backing layer, and said shaft of said stud passes through said pH-control layer and said backing layer to enter said open end of said snap fitting.

11. An active electrode for driving medicament into the skin of a patient from a solution of the medicament contained in a reservoir on the therapeutic face of the substrate of a transdermal medicament patch, the reservoir being disposed interior of the periphery of the therapeutic face of the substrate, and the reservoir electrically conductively engaging the skin of the patient when the therapeutic face of the substrate is disposed there against, said active electrode comprising:
  (a) a planar backing layer positioned between the reservoir and the substrate and comprised of an electrically conductive material, the surface of the side of said backing layer remote from the substrate defining a driving face of said backing layer; and
  (b) a pH-control layer on said driving face of said backing layer covering less than all of said driving face, said pH-control layer and the portion of said driving face free of said pH-control layer together electrically engaging the reservoir, said pH-control layer being comprised of an electrically conductive material capable of moderating changes in the hydrogen-ion concentration in the reservoir, when said patch is disposed against the skin of the patient, and an electrical potential is imposed between said backing layer and the skin of the patient at a location remote from the reservoir.

12. An active electrode as recited in claim 11, wherein said pH-control layer is comprised of a material capable of precluding electrolysis in the reservoir, when said patch is disposed against the skin of the patient, and an electrical potential is imposed between said backing layer and the skin of the patient at a location remote from the reservoir.

13. An active electrode as recited in claim 12, wherein said pH-control layer is comprised of a mixture of silver and silver-chloride.

14. An active electrode as recited in claim 11, wherein said pH-control layer is comprised of a material capable of neutralizing electrolysis products in the reservoir, when said patch is disposed against the skin of the patient, and an electrical potential is imposed between said backing layer and the skin of the patient at a location remote from said reservoir.

15. An active electrode as recited in claim 14, wherein said pH-control layer is comprised of potassium phosphate.

16. An active electrode as recited in claim 11, wherein the ratio of the area of said portion of said backing layer free of said pH-control layer to said pH-control layer is in a range from about 0.20 to about 8.00.

17. An active electrode as recited in claim 11, wherein the periphery of said pH-control layer is geometrically similar to the periphery of said backing layer.

18. An active electrode as recited in claim 11, wherein said pH-control layer comprises a plurality of discrete, unconnected pH-control layer components covering a corresponding plurality of discrete, unconnected portions of said driving face of said backing layer.

19. An active electrode as recited in claim 11, wherein said pH-control layer comprises a single, connected layer having an aperture formed therethrough, said driving face of said backing layer being free of said pH-control layer at said aperture.

20. An active electrode as recited in claim 19, wherein said pH-control layer has a plurality of apertures formed therethrough, said driving face of said backing layer being free of said pH-control layer at each of said plurality of said apertures.

21. An active electrode as recited in claim 20, wherein:
  (a) said pH-control layer comprises a field of intersecting grid lines; and
  (b) each of said plurality of apertures is bounded by plural of said grid lines.

22. An active electrode as recited in claim 11, wherein:
  (a) the periphery of said pH-control layer coincides with the periphery of said backing layer; and
  (b) said pH-control layer has an aperture formed therethrough, said driving face of said backing layer being free of said pH-control layer at said aperture.

23. An active electrode as recited in claim 11, wherein said pH-control layer is disposed interior of the periphery of said driving face of said backing layer.

24. An active electrode as recited in claim 23, wherein a portion of the periphery of said pH-control layer is tangential to the periphery of said driving face of said backing layer.

25. An active electrode as recited in claim 11, wherein a portion of said pH-control layer extends exterior of the periphery of said driving face of said backing layer.

26. An active electrode as recited in claim 11, further comprising an electrical contact electrically coupled to the surface of the side of said backing layer opposite from said driving face thereof.

27. An active electrode as recited in claim 26, wherein said electrical contact comprises an assembly of:
  (a) an electrically conductive snap fitting; and
  (b) a stud receivable interior of said snap fitting.

28. An active electrode as recited in claim 27, wherein said stud of said electrical contact is electrically insulative.

29. An active electrode for driving medicament from a reservoir carried on the substrate of a transdermal medicament patch, said active electrode being positionable during use between the reservoir and the substrate interior the periphery of the reservoir, said active electrode comprising:
(a) an electrical contact;
(b) a pH-control layer comprised of an electrically conductive material capable of moderating changes in the hydrogen-ion concentration in the reservoir, when said patch is disposed against the skin of the patient, and an electrical potential is imposed between said backing layer and the skin of the patient at a location remote from the reservoir; and
(c) an electrically conductive backing layer sandwiched between said electrical contact and said pH-control layer, the surface of said backing layer contacted by said pH-control layer defining a driving face of said backing layer, and said pH-control layer covering less than all of said driving face.

30. An active electrode as recited in claim 29, wherein said electrical contact is electrically coupled to the surface of the side of said backing layer opposite from said driving face thereof, and said electrical contact comprises an assembly of:
(a) an electrically conductive snap fitting; and
(b) a stud receivable interior of said snap fitting.

31. An active electrode as recited in claim 29, wherein said stud of said electrical contact is electrically insulative.

32. An active electrode as recited in claim 29, wherein said pH-control layer is comprised of a material capable of precluding electrolysis in the reservoir, when an electrical potential is imposed between said backing layer and the skin of a patient with the medicament patch disposed there against.

33. An active electrode as recited in claim 29, wherein said pH-control layer is comprised of a material capable of neutralizing electrolysis products in the reservoir, when an electrical potential is imposed between said backing layer and the skin of a patient with the medicament patch disposed there against.

34. An active electrode as recited in claim 29, wherein the area of said pH-control layer is less than the area of said driving face of said backing layer.

35. An active electrode as recited in claim 29, wherein the area of said pH-control layer is equal to the area of said driving face of said backing layer.

36. An active electrode as recited in claim 29, wherein the ratio of the area of said driving face of said backing layer to the area of said pH-control layer is in a range from about 0.15 to about 1.00.

* * * * *